(12) United States Patent
Yoon et al.

(10) Patent No.: US 9,540,616 B2
(45) Date of Patent: Jan. 10, 2017

(54) **METHOD FOR PREVENTION AND TREATMENT OF *SALMONELLA* INFECTION**

(71) Applicant: iNtRON Biotechnology, Inc., Kyungki-Do (KR)

(72) Inventors: Seong Jun Yoon, Seoul (KR); Sooyoun Jun, Seoul (KR); Hyoungrok Paik, Jeollanam-Do (KR); Gimo Jung, Seoul (KR); Yoonsik Shin, Kyungki-Do (KR); Sanghyeon Kang, Seoul (KR)

(73) Assignee: INTRON BIOTECHNOLOGY, INC., Joongwon-Ku (KR)

( * ) Notice: Subject to any disclaimer, the term of this patent is extended or adjusted under 35 U.S.C. 154(b) by 0 days.

(21) Appl. No.: 14/934,920

(22) Filed: Nov. 6, 2015

(65) Prior Publication Data
US 2016/0053234 A1 Feb. 25, 2016

Related U.S. Application Data

(62) Division of application No. 13/176,458, filed on Jul. 5, 2011.

(51) Int. Cl.
*A61K 35/76* (2015.01)
*C12N 7/00* (2006.01)

(52) U.S. Cl.
CPC .............. *C12N 7/00* (2013.01); *A61K 35/76* (2013.01); *C12N 2795/00021* (2013.01); *C12N 2795/00032* (2013.01)

(58) Field of Classification Search
None
See application file for complete search history.

(56) References Cited

FOREIGN PATENT DOCUMENTS

KR    10-20090030385    *   3/2009

OTHER PUBLICATIONS

Machine translation of KR 10-20090030385, 2009.*

* cited by examiner

*Primary Examiner* — Irene Marx
(74) *Attorney, Agent, or Firm* — Meunier Carlin & Curfman LLC

(57) ABSTRACT

The present invention relates to a composition comprising bacteriophage SP-1, the bacteriophage capable of destroying *Salmonella* once being infected in *Salmonella*, as an active ingredient, and a method for prevention and treatment of *Salmonella* infection using the same. Bacteriophage SP-1, the active ingredient of the composition of the present invention, characteristically has the killing activity to *Salmonella* and has the genome represented by SEQ. ID. NO: 1.

2 Claims, 4 Drawing Sheets

SEQUENCE LISTING

<160> NUMBER OF SEQ ID NOS: 3

<210> SEQ ID NO 1
<211> LENGTH: 43285
<212> TYPE: DNA
<213> ORGANISM: SP-1 bacteriophage

<400> SEQUENCE: 1

| | | | | | |
|---|---|---|---|---|---|
| aactcgaact | gtgcggctgc | gccgttgtcg | ttagtaatgg | tgaacgtgtc | gataagttta | 60 |
| agtggcgcgg | caccgtcata | agcagataca | tcaaccgatg | caaacgggcg | ggcactaaaa | 120 |
| ttagtcgtga | agtcggaacc | gctaggcggc | gcctgtaaga | tttcctgatt | caagccgatg | 180 |
| aacgggaatg | aaccggtcac | cattgcgtta | acagcctgtt | cgatagtgaa | cccggtaaac | 240 |
| tcgacaccac | gggttacgat | gtatgaatcc | gggtttccgc | atttaccttt | caaccatgtg | 300 |
| aggattgaat | aggtcttaca | caagttaccg | gtttccagtt | tatctgcgat | acgcaaatct | 360 |
| gcctggacgt | cggattcggc | ggtaagggta | tgctggatgc | ccgcaccggt | tacgaccgta | 420 |
| gccgttactg | cggtaacgag | gaaagcttta | tcgttattac | cggacaaacc | atcgaattgc | 480 |
| accaggtcgc | ctacttcaac | gccatcggtt | acaaagctac | cggaggcccg | tgtgaaagtt | 540 |
| ttcgctaccg | ggtcaaccgt | aatgccgatt | gccgatgcgg | tggaacctgc | tacccatgaa | 600 |
| ctggtcattg | caccggctaa | cagctcgtcc | tggcttgtcg | cgcttagttc | gatagcgtat | 660 |
| tcaccagtta | cctgacggtt | accggtacgg | atggatgatg | tttcgcggct | gccgtccagc | 720 |
| tcgttagaga | tgagggcgtc | gcgcgttacg | gcggggatgc | cacctgtgtt | gcggagtggc | 780 |
| tgccataccg | ggttagccgg | cgtcacaccc | ggtgttgtct | caagtacgta | aaattgcgcg | 840 |
| gtcatcgcgc | ctttgtatgg | ttgtaacgcc | attatctaat | cctcgctgta | aaggctatga | 900 |
| aattaattga | gagaggcctc | ttcgcccatc | cattctcaac | aataagagga | ccgaggctta | 960 |
| ctgattgtac | ctcagcacag | atttcgttac | gactaaaaca | gttaccggcg | gcgaaggcgg | 1020 |
| cgtttagctt | atcagctaat | cggttaatag | gagcgctacc | caaggccgac | ccgacgttaa | 1080 |
| tgtctacctg | ataaacaccc | gcccgttgtt | cagtccaaaa | caagtcggct | tgttctgtat | 1140 |
| cagacaacag | catataactc | gcgatataag | gtgcgtctgt | agacgtcggc | gcatcgatgt | 1200 |
| tctctaatgc | gaccttgatg | tcgttgtcca | tgccgaacgt | caccagcgcc | gtgtcgaatg | 1260 |
| ctttcgttaa | gtcctcaaaa | tatgttgcca | ttatttcacc | ttagaggctt | cttcatttaa | 1320 |
| tagttgctgg | aacctgctaa | cgttaactct | aacgaatcct | tgcggggcct | gttgagacca | 1380 |
| accgtactcc | agacgttgcg | catacggcaa | attgttagta | agggtgaagg | tgtgccagtc | 1440 |
| agcagcattt | agaacgaaac | ttgtaacttt | accggttgct | gtgttgccgg | atttatcagt | 1500 |
| agcgtccgta | gttccttcgg | cgggggtgct | tcctgaagcc | atccagttca | tacgaaatcg | 1560 |
| cccggtatct | acgggactcg | ctttgataat | cgcagaaaac | aactttatag | aaacctgacg | 1620 |
| aattaccttt | tcaggattct | tcttagcctt | ttccacgaac | ttggacacat | caagcgcaaa | 1680 |
| actcattttc | tcacctgaat | aaagtatgcc | acaacgtcat | cgttaaccat | cttcttctca | 1740 |
| atagcaacta | cagaccattg | ttcaccgcta | aaccgaacct | tgtcatccat | ctttggcact | 1800 |
| acgctgtaat | ccgctttaac | catcatgtcc | ccggcctgaa | tggtggtccc | gtttacaaca | 1860 |
| ccggcattaa | caggtacagg | aaccgcttta | agagggagta | cgacgtcagg | ccccacacg | 1920 |
| tactccccta | aaacagggtc | ccaatgtttt | ttggcctttg | cgcaccaaag | ttaccgtgct | 1980 |
| gccgtatttt | ggtagtaggc | gagtacctac | gccttgcatc | cgtttactaa | aagcggtgcc | 2040 |
| cattacacac | cctccagtct | tgagatgacc | agcaatgcgg | atggagctac | accccaggaa | 2100 |

```
gtaaccgttg ccgcttgtgg gtacagtcca ccgaagttag aaccggcggc gtcgcgcata    2160
atctttaccg taaaagtttg cccggctgcg gcattcacaa caacacgaga ttcaatagga    2220
acagtaacat cggtgctagc cagcttagcg acggcgggtg aaccgaattg agcgccggcc    2280
agcagaaccc gcgacaggag gatagaggtc ccgctcgccc cagtccgccc ggcctgtaac    2340
ttaacacgga tggcatagtt acccgcggca ttaaaacgta actacacccg acgcgttaat    2400
cattaccggg tcagcgcttg ttttctgtgc cccaccaaag gctacggtta atgctgtacc    2460
tgtggtggtc ggtgcctgaa tatctgtaga cgacgcgcgg aggacctcta cttccttagc    2520
cccgtacagc atagaatccg ccatctgagt ggtaacttcg cgcaacttttt ccggtgtaat    2580 tagcccggac tggttatcag ggaagtttgc cccaattaag gcgaatattt ccgatttagt    2640
cttagccatg tttagcccct aaaaacatta aaggagtagg cattattgct accgcataag    2700
agaggtcgta gcgcatcatc ggctgccgtg atgcttactg tgccgcctga gtagccattc    2760
ttaaagtagg acaccgttac tgcaccctca acccgttcgg tctgaacctc tcgcccgtct    2820
gtagaccctc gaacgtcggt accagcgcca tactcgaccg cggccattac ctgagcttga    2880
ataactaacg atggaattac attggatggc tgggggaacc cgtgtaaagt aacaccggtt    2940
cgagggaatg ccagtgcctg gtttgcggat acgcgacgac cgcacatctg agactcaaaa    3000
aggccaacat ataccgcgcc attacggaga gaggcctccg ctgcgatgtc atcttctggc    3060
agctcaagac cgtacttaga ggccatggac ctcgcgtctt ccaggctgac gtaagagtca    3120
gcattcggga tgccttgacc ggtttccacg ataagcggca taattattc ctctacgctt    3180 ttgcggcgac gacgctgctt aggttctccg ccgccgttgt aatgcggttc ttcggccact    3240
ggctgatttt cgattaatgc ttccgggttc gcttcttcgc gcatcgggac taactgcccg    3300
tcaacctcga ccacacctttt gtattgttcc cgtactacgt aattatctgt catgtctaat    3360
ccttaaagcg gcccggaggc cgcatgtatt taacttactg tcactacagt actatctgaa    3420
atgatattac cgtagccgtc gtgcgctacg actttgtaag taccggaatc cgccaccgag    3480
gagttggcct tagtgtaagt caaagcggtt gcaccagcga tagcgttatt atccttatac    3540
cattgaacgg ttttagggtc catgccgtcg gcgagtccca cggtcagtgt gatagcctga    3600
ccagtggtta ccgcggtagt atcattgaga ccggtagaga aacgcaacgg cattacgttt    3660
tccatatcaa tctcaacctg cccatcctgc ggactatcat cagacacacc aacaatacgg    3720
cgtttaatta catcaaccat ttttatcctc ctcaggatac agtaccagcg ttttttaagag    3780 cggttagcag attagtaacg gcagtgcgca atgaagtcac atctgtacgc aacttattgt    3840
agttggtaac cagtgcatcg aactcttctt tcgtaggagc agccgcggcg gcggccccac    3900
tacccgcgct aatcgccggt ggtgccgcta cagtagcaga tttttttaacc cctccgattg    3960 ccgttgtggt ggcggcgggg atatcgaact ccgcgttaac caggctgcgg ggtagccctt    4020
tacctgtctt tgacattata ttgcctccgt ataaatgaaa agagggaccg aagtccctca    4080
agagtatacc ctacgtttaa gcaccgacgc cagttaccag gaacgcaatc ggtacgtgct    4140
tacggtcaac tacacggttc cagttggtag cgttagccag gtcttgccag ctagcggagc    4200
gggcgatagt ctcagtaccg ttgccggtga ttacggcgct ggtgaagctg taaccaaacg    4260
gatgcagcaa ccacgtttta cgcgtccata ggggtttcaa cgccgccgcc gttagcgcga    4320
gatgcttcac gctcgtattc caacggcatc tcaggattgc cttcgccata accgatagcg    4380
ccctggccga agatgacgga gatgaacttg cggctgcgca ccctggccta ctacggtcat    4440
```

-continued

```
gctgtcatcg acgataacac ggtagccctg gtaggtggcg aacatggtgt tgttctcagc    4500
gtcacggatg aagtcgataa gctgagcttt acgcgcctgc gcatatacga agctgtgcat    4560
cgcgatagca ccgagaacct caccaccatt acccatcaat gcgtcaccca tagtctgggt    4620
agcgtcaatg aatgcacctg cgtcgaagcc tgaagttgca gaaacgtcga ccaccatgtc    4680
gttctgcttg tgatatgcat cagtagcgga tacgttgtcg ttgtacagac cgagggcggt    4740
agcaatcaga cgacgctggg cctggcgctg ccagaagtta tccaggcggg aggctacgga    4800
ctgcaatgga ttctggctag tcagttcgac agtcaggtct gcctggccga aaccttcgtt    4860
cagatacgca acgcgggcca tcatttcacc ggtctgaata gcgcgcgggg tagcaatatc    4920
ctgatacaca tcgttcgaat agttaggttc gatagaggta tcgatggctt tccagaacgg    4980
caggttagcg atgttagacg ggccgcgggc aatctcggca gcatacgcag ttggagtcaa    5040
aattccggag ttgaaaaacg cggttttctc taccgggtct tccgtcatat aggacgccag    5100
tacagggata ttgccagtta cgatgttgcc aatagtggta attgccatta tttatttcct    5160
cagggcttta agttgccgtt caaattcggc agggttagat ttatagagag ccaatcgctc    5220
gctttcactc atgtctttaa acgctggtgc ggccccgccg cctttattcc cggaagcccc    5280
gccaccggaa gctgcatttg ctttaatcaa atgtgaaaaa gctttatgtt cgcgcaggta    5340
tttgcggaat tgctcagggt cggtagtaac aacattgcca tccgcaccca tgaatttagt    5400
cactacgtct tcgccttcaa actcggtctt aacgaacggt gccaggattt ctaccgcttc    5460
tggggtgata aaatcaccag cgaaagaacc taaaacagcc ttacgttcgc taccaagaat    5520
acgcgccgct aaagatgcgt aacgctcttc tttctctttc agtacaggtt catactgact    5580
acgaatcgtc ttttcaaatt cgtccatttt accggcggcc ttcaaggctt cctggtgggc    5640
gcgttgccgt tcttcttcgg cttctttagc ccggcgcgca gcttcctttt tctcgttaag    5700
gagcgcttct tgattcgcct taagcccggc cacttctttc tcaatcagtg cccgcacttc    5760
ttcggctgtg tacatttttg gtgcgtcacc cgcacccaga tttatcttcc accccggctt    5820
cttcatgaag cgggtaacgt aaaaaacgat tcatagtcaa tatgtcccct ggactttagg    5880
acaccgggcc acccggtgtt tctgtaacaa gaataaatta ttccacttac taaggcaact    5940
attccagaat attccttatg tactcctgca accggaatac tttcaggcgc aattgccgtg    6000
tgcactcggc gttctgtacg tcgacggcca ggtcttcatc ggcatcacta cttggtagca    6060
ccattttgca cgggggctgc atcaacgtcg tatccgggga tggaattagc attctcagtg    6120
gcgcgtcgtt tgattgacac ccgttcagaa ggaaactcgc agacagtacg gccaggacgg    6180
ataacatatt tgatgacttc atgggtgata gcctccgaat tttctttgcc ttccgattcg    6240
gcggaggcgg ccttagtatc attctgctgc tgccgttgtg ttttcttcgt cagctcagct    6300
tgtgccttct tttgttgctg tgaaacgaga ttggcgcggc cttctaccca cccgcttctg    6360
tagttgtact ggccgtataa ccacaaggag aggataccgg ctgccgtggc taccgcggtt    6420
actttccaat tcatagtatc cccttttcttt atacgctaag cccgacgaag tcgggcgtta    6480
atctcgtata tctgtaaaca tcatacggcg aatcttagct aaatactgaa agcaatatag    6540
ctcggccctt ccgaatgcgt tcgcggttac gctagggcgt tgtgacgccc gcttcacgcg    6600
acccgcaccg cggtacgctg aaagcgtagt tagcgtagca tttaaaataa tagaaatcta    6660 cttttttgaat aaagtattcc tgaatttaca ttggtaagga ataactggaa taatcgctgg    6720
taaaattaag gccccgtcaa ggggcctttc gttacttagg ttctgagacc ttagccgctt    6780
tgctaaccac cgacacaccg tcggcatcta ctgccttgac gaaatattct ccggggtctt    6840
```

```
taacggttag ttccccttca acgtaaggaa cgtttattac ctctttacca tctttaaacc    6900
attgcaaatc gtagggcgct ttaccgcctt ttacaactac ggttaatttt gcagaaccgt    6960
ctttcagctc tacatctgcc ggttgcagat cgaagtacac atctcccgca ccatccagat    7020
acggtacttc gtacaggatg ccgtctgaga ttgtggtcag tccggtctta tccgcaaacg    7080
gcatttcatc taccgactcg ccgagaacag attcgtcttt aatataaaca acgccttcac    7140
ccgcaccaga cacacgtgcg tactgcacta ctcgacgtga cggcacatct ttaactttga    7200
aaaagcccat ctttattcct ctttcagata atcggcaaca cgtttatcga gctccgccat    7260
ctctttaaga gttaacgggc gcccgaatcc gtctaccgat attacacgaa attcttccgg    7320
tgttatccca ctattacgaa aaatcttacc ccttacgggg ccaagtgctt cgtcctggaa    7380
ccacgccggt tgttgtttaa ggaattcgta gtagctcgtg tccgcgctta cctgctgacc    7440
tccatctgca cccctggccg cccgttttgc acccttatcc aggaagtcga attctggact    7500
tattaccggt gctgtgctcg accgacagtt aggatgcgct ggcggtagcg gacctttacc    7560
tatttcgtat tgcatagaat cccgcgaccg acaaacggct gaggttctgg agtcaagggt    7620
agatacccac tcgtatttcg tgatgatgtc gccgttctga gcgtaaacct gttgccgtgc    7680
ttcgttggat acgtgcgcca gcgctgtccg gataacggtt gcagcgttac gctcggagat    7740
atcggccaga ccaccgggcc cgacaacgtt cttaactatc cgacgtgtgg tcatcccctg    7800
tacgaaccca gatttaacgc ccataacaag gcgatttacc tcggtttgcc gccagccgct    7860
cattagagaa acaaaatcaa ctggcttttc gcttagttca agaggcgcga aagttgcggc    7920
ggcccatact tgttcggcgg ccggtgttac gaaattagcg ttaacgttgg tcgacagggt    7980
ttttacgttc cagttaactt catagtctga aagctcacgg gcatcggcca gtagcttctc    8040
ataccaccca gacgtaatcc cgttcagcgc ttgctcaagt tcccgcagca tggtggtaag    8100
tctcgccgcc gttctgctgt catcaccaaa caacaacacc tgccgcttaa cctcatcgcg    8160
catctgcttg atgaatggcg ccaggtcttt cacctctccg gatgcggtgc gttgtaacca    8220
tacctggtgg cttattaatg atgtaagtaa gctcatagat aaaccctgtg atgctaaagt    8280
taatagcata ctataagaaa acccatccca aggctatggg cgaccctaat tagtagaaca    8340
acttaatcat agttctaaag ttaactagaa gtatttgacg aatactatat ctaggtggta    8400
gtattcattc aatacttcaa aaaggagata gaaacatgaa atcgcaaaca ctagaatttc    8460
cctatgggga tataactttc accccgagaa ggtgagctga acctgacggt attagtgaag    8520
cagatgaata agtggcgtga agaaaatggg atgggtgtga aaaacctatc gcagctgtta    8580
tctaccgagc aagccaggtc gttcgcgcgt gtgtgctgtg aggaattagg gatagaaagc    8640
gcgtggcgtg tggttagagg gaaaaacgcg gcaacatacg catgtctaca tatggctata    8700
tgggttgcgg agcaatattc tgactattac cacttcctcg ttatagaccg tttcttaact    8760
caacggcagg tagaactccg taacattggt gctgttagtt ttgtagaact taatgccgcc    8820
gttagccgga tgattgagcg tacggagggt aggattgggc gtatcggtca cttcatacat    8880
gtggcgaatg cgataaaaga gtctatagat atccgtgaag taaccggttt tgatacttgg    8940
gactctcagg acgccaaaac taatcaatta cggagtgata ttcaaaaggc tatggtgacg    9000
ttgttggata tggaagcagt caactcatgg gatgagctga aagagacgat accgcgggtt    9060
gtgcgtaaat gcgcggctaa tatccgctaa aactaaggcc ccgtaatggg gccttttttct    9120 ttactcctgt tgttgttgtg ccgcttgcgg aatctccccc gctacctgag taacagcacc    9180
```

```
cgacggcaaa ggtgcatctt caatagcgtt cagaatatcc tcgtcggtcc agtcagtcac   9240
ccccgcctta cgcaacgcag cgtaataagc agtggcgggc agtaatccgg cattaatgtc   9300
tgccatccac gcagccctgt cctgtgctgt cataggttgc aggaagaaat ccatgttaag   9360
ctggaactcg acttcagaat cttctggctt acccaacatc atagcaaccc atcgtaaagc   9420
atcggtatac gcctgactta cgttacgagc gattgtggcc ataacggatg tatcggcgcc   9480
gcgttggatg cgcgcggatt ctgcggtaat ttgctgagat ggtgtaataa gttgggcacc   9540
aatctggata gcctgctgtt ctttgtccag catattctgg cgggccaggt tgttttcgcc   9600
cgcctgaata agttgagcgc taccaccata accaaggtta tgcccgcacc gactgccaaa   9660
tttgatgccg ttggggttgg cttccttgaa cgactgtggt gtaaggttat ccccggggta   9720
gataaacagc gtaggctggc caactacaaa acttgattcc tcgttatcag cactgttccg   9780
gtagtgcccg atattaagct cggccaatgg caacaaagga gcgtcgtcaa tggtggcgtc   9840
gttattggta gctccgataa aggtaaacgg aattacgcca cgtaacgact cccctaaatc   9900
tgggtaaatc tccacaacct cttcctgagc tccgccttcc gcatcgaaac ggaacagtcg   9960
ctgacgataa ttaccatcgg tgtcaatgtc cagcacgcgg tactgctcgc cgtatttagt  10020
ttcgaactcg tttccaggtt cgtggtactc ccatgtctca cgcagcacaa ccatagttac  10080
ccggtttaca gaacctacgc gcgtgagtcg ccagttaacg atattctcgg tagtgtagaa  10140
agcgattgta gggttaagca agcccgcatt ttgttcggca gcggtggccg cggctgtttc  10200
cggagcatca acaagaagac caccacgacc tactgagtca atctccatga gtgtatcttg  10260
cgcgtgctgt attaggccta caccagaccc atctgcattt ttaagcaggt attccagctc  10320
cttcggaata ttgatttctg gttctttgcg catgacgcta ccgaccattc ccgacagcgt  10380
tcgccgggtg aagttgtaga cgataccccc ggcctcgtat tctgcctgac gcgcttcgcc  10440
gtatgcttta tctggttcat taaggccgac gttgcgtaag tagccaacca ggtctccagc  10500
aagcgcatgg cgcaccttct gccatttcgg cgcgtagtgc agccattcgc ggtgcttggt  10560
ttttacgcca gaaccctggc cgtttgctgt taacatttaa taatcctctt aaagtgcaaa  10620
agtaaccggg atatgggaaa caggtttaac caacggcatt tcgtaggcga tagggtatcc  10680
tgtcgcgtcg ttctggtggt cgttgccgct tgtcttatcc ggtataccgt ttttatcgta  10740
agcctgttgc tccaggcaac gtgctgtaac cgggcaagcc tgctcgttga ccattaatct  10800
accagactcc agcgctttat tcaccgatgc tacacggtct ttaaccgcag ggttaactga  10860
tttcgcacgt atctcgaaac ccgcgttctg taattgggca atatctgacg tactggcatc  10920
agtcgattta cggttcttgc cgctggcatc cggatacatg acgatgtggt ggccctgtcg  10980
cccccatcgc tcggtaattt ccctgaccac atccggggtg tcgaacatat ccaccagctc  11040
ggctaccgcg tgccagacat actcacgctg aacgtatacg gtgctagcca tatgcccgac  11100
gttgaagtcc tgaccgatgt acagcgtctc tccaggttgt atagtctccc gactgctgtt  11160
cttacgtcgg tcgtaagcat aatacacgct gccggatgtc aggttgacaa attgccgtc   11220
gatgtaggca tcaattaact ggcctggata cgtatcccgc aacgactgca cataatcttc  11280
cggtagaaag ggattggatg ttgtcgaggc ctgaatcatt tcatagcctg gtttctttt   11340
tacagcccat ctgtcgtgca caaaacggaa gccttctggc gtcgtaaata ccgaaactgt  11400
attagcgggc ttcggggtaa ttggacgata tgtacgcggc aactgacggt tacgggcgat  11460
aactttgttc caggcgtgct cggcgtggtc tttatttaac gtgtccaact cgtcgatttt  11520
tgcgcggaac gattcgtagc caacaattcg tgctggatta tccaatgtgc gaaggacaaa  11580
```

```
atcctcgaat tgcccgaatt gcccggatga ggtataaatg atgttgtcgg atttattata   11640
cttgtagcga ataccccaat cagacaactt ctcttccata cgcggagcga ggataaggcg   11700
caccaggtcg tatgtcggtt catacatggc gataagtgaa tcactaccgc cctccatgct   11760
gtcgagtagg gcggaattgc acatgacctc tgatttacct gtgccgaagc ccgcaacgaa   11820
ggccgggaac ttacaatgca gattaaggaa cgcgccttgc ggttccgtag ctgtgatatc   11880
aacgttcacc ggacaccacc tttaatagtt acttcgctaa ttggttcgtc gcgcgcttct   11940
tccacaacag ttttattaag ccccagtttc gccgcggcaa acgtagcgga tatcccggct   12000
gcaccggtct cagtgaaata cgcctcttcc agggcttgtg ccgtctcata tgcttcggcg   12060
aatgcaggaa cctctcggag ccatagcttg ataatcggga tggttacgcc gatgtgtaat   12120
gcgaagcggg ccagcgacgg cggtttgtcc tggataagcg ggcgttcgtc gcctttagac   12180
gtgggtacga gttcccatga cgcgcggtcg aagaacctga ttaactcgtc gcaatagtcc   12240
ggatcccata gttcggcgga atgtctggat gactgataca ggctttgttt accacgcggg   12300
cgtttacggc gacggtttgc actaaccgct tcttcgtgcg cggcggccac tacttcggcg   12360
tcaggctgtt ttaatttgag tttcatgcaa tcctctctta aatgcgtatg accatcatag   12420
cgcatcagac gcccctgag cgtctattaa ggattgtaca ggggaatgaa ggcctgtgta   12480
cagaaaagcc cgcagaagcg ggcttgtgtc agttatatag gccgtgtcgt agtgctcttc   12540
taccatcgcc gccgtaatgg tcgttagctg cggcgataac ccaggcgttc gggatgatta   12600
gcaatctcat ttgaaaaacc acagcaggat gccggccgct cctgatacac ccaagcctaa   12660
aaacataggc caccacagat atcagggaag actgttaaac acagtcggtt gttttattag   12720
cgcactgaga aaggcaaacc aaaacatcag gtcgccagtg gcatcggtag ccttcaaaat   12780
ctcaatcatt ctccactctc ctctttataa acccaccatt tacctacggc ttcccatcgc   12840
cacccgcgac tatgtatggc ttcgaaccta cgaccaaata ctgtttcccc gtaccacatg   12900
acaaatagct tcaccgcggc accagcacca gctttatgag cattcaaacg gcgatacgct   12960
agtgacatcc tcgtaagact taccgcctca acaaatggcc aaagaaacaa aatccacatc   13020
aggtacatag caccggcaag cagtaatgtt gtgaatccta tacccatgag gatgagaaaa   13080
ctatccatca cccctccagc ttcatacggt cgttgcgcga taatccacgt ttcgtgtaga   13140
tgaccggtga cgttttcgta tgggtcatca gtcggttgtt atagatgaca tgttgctcgc   13200
attttgtgtc atggcggtac ttggacaatg tcatctcatt aagtcccgtc tcccggcacg   13260
tatcagccag cgtgccgtgg gtctctatta gttttgggat actagtaatc attcctgttc   13320
gctctccttc tcaagtcgtt ccagcagcat cttgtatgct tctaactgga attcttcgtt   13380
cattgacagg cccagcttac ttacagactc caaatacgtg atgcgttggc gcaacgtttc   13440
tttgcatact cgtttcatcg tttaatcgcc cccgcactta acacactgtc cgcacatatc   13500
tttaggattg ttaacaaaat cgtgctcgca cttattcagg tcataacggt tgataagctc   13560
ccggcgatac tcattaaggt agtcaagcgc agcctggtgt gcctcgalltt gcgcgtctac   13620 tgcttcaatc ttaaacctgc cgttggcggc ttctaccatc atcttttcat attcgttgtt   13680
agtcatttct tcttacccca cattcgattg agatacttgt tcttgtccgg tcctgggaaa   13740
ctgttacgtt taatcagttc ctcgcgtgtc gggaagggcg tgttacttac cttaccgccc   13800
accttaaacg ttaccgttac ttgcccgttg tcgctcattc ctgcacctcc catccgagta   13860
catttacgcc gtcatagtaa tgtgaggtgc gctccagctc ggcggcggct tcggccttt   13920
```

```
tttcgctgag ataaacatca agaacgtaag tgtccccgtc gtgatgccat cccggatacg   13980
atatatactt tcattttgt tctcctgcat aagctgcttt cagtgtctgc atcgcggcga   14040
accagaacgc atccgctgga atccgtgtac ttaggttatt aacggcaatg cgtgccatca   14100
gttgtgcgtc tttgaatgct tcggtgtcca gtagcggttt gcaatggtaa aaaactttat   14160
cgctttgtaa gttcatcttc tctactccgt tctcgttgtc gatgaactaa atataatagg   14220
gttaatgtta ctagtcaact attatttctg aatacagata aaaaaaaatc ccggtaaggg   14280
tcagttaccg ggataaagga gctagaggga tgaataagca ggagcgacac cagtatctta   14340
ggaatgctcc tatgtgtcaa cctactttgc ttcgcggccg atggcttccg cctgttgcca   14400
cggcataccg tcgaatagcg caacacgacc cgcggcacgc cgacgcaatc caaggagtga   14460
tttgccgttc tgataatgga actgagatag cttattccgc agtgtggcaa cgtcgccctt   14520
acgcagggcc tgccctgttc cggtagaagc cgcaatcaca ccggcgccag cgttatacac   14580
caggtcgcac atcgcatcga actgtgactg attgagcgac ggatgcgcta cagcgtctac   14640
cgcagctacg gccttagcca tatccttgtg cagcagcaga agaccctgtc cctcggtaat   14700
cttctggcct tctttcacat ctgcgccgta gtggccatag ccgatagtaa gtacttctca   14760
ctcttcgttg ccttgtacgc ggttccgcgg aaaccttcga acgcggcggt gaatttgatg   14820
ccgttgttac taatgtttcg gtttgacata catcctccgg tatttgtagt agcgagcgcc   14880
tttcacgcaa atgtgacgca ccgatttaag cgcgaatata gcgacgagag tcgtaattat   14940
gaacggtgga atggcaccgg taaagagatg ggcgagacct ccggcggcgg tcaccaccga   15000
cgccatgtac agcaggcggc cgaaaagacc gtcttcaacc cagtcggcgt agatattaat   15060
taacgaggtg gcgatgatgg caaccaggca aatgacgcca attgatgagt tgagcatgtt   15120
atctccccca cggtaactta agttgctga gggatgagtc agcagcttcg aataacttaa   15180
gccagaacat acctaccccg aaaggaacca ggtactgacc ctcagactgt gataatttca   15240
tagtaactta taatgatggg ggatgcgtac actgcacaac aggcggaagc ggtgagatgg   15300
cacaatcgca accatggcga aatagcctca cgcttcttaa tctgagatac ggcaccccg   15360 gcgaggcccg ccacactaag ccaaaggtat ttatcgtcca caataaaaaa tctccgaaag   15420
ttggtttatc cttcggagat tagcatttat acgacaattt tagtaacaga taattcggat   15480
ttatcctagt cgatgtgtta tcacgcttcc atcggtacca gggtcaaacc tcttcgcaac   15540
ctctaccgct tccgttgccg tcgcgcccat gaacatggct gtaagtgcat acggagcccc   15600
ggagcctacg gcagcagcgt tacctgcaat tggtataacc gagcttaacg gtgcgtccca   15660
cgccctacag aattctaccg cgaaaatacg gttatcctct ttaacaaaca ccagcgccga   15720
aaagtcgaag tcgtagtgct taggcgtcag tatctcatca tcggcaacca acaacatacc   15780
caccccggcg tccccggata cccctataac aaagtggtcg ttctcgtaaa tcttggtatc   15840
cgtgtggtat ttgtaattgc cggtgacaca ggtatcacag gccatggttt tgccgtcgaa   15900
agctatcgta gtcatataaa ttacctgaac gtataaagtc gaatagatgg cttgtgcggg   15960
atttcggaat acccacgttt acgccacagt ttgtacagtt taaccgccat atgcgccctt   16020
gcctggctac tgaactcccc caggtttacc actttcttcc cgtcgtaaga gtgcgcacgc   16080
cacagacctt tgcctacaca atacttaggc tggtgcaccc cagggatgcg cggatacacg   16140
tccggcatct cattaactgg ctttgcgcgc ggtttaggtt tacgcttaac ctttctttta   16200
acgcgagtaa ccttctttgt taccgccgat gaaggaggtg ccaggttgat gccggcgtgt   16260
ttcagtatat cggttgcgag actcatttct cccctgctt agataaccgt ttcagtgtgc   16320
```

```
aaataccgcg tacctgagcg tcaacaggac gctctacgaa agttaacggc gcgttctccg    16380
cagcgcgtgc ggctacctgg cacgcctcta acgtataaaa cgtttctgtt ccggcaagtt    16440
gtagctgacc cgcggataca acccatatga aaagtatact tgtcatttga ttatcctgta    16500
cttaactata tcccagttgt tgttatcaat cccccaccgg tagtcctggg ctgcgccgac    16560
ggctatagag ccattgcgga attcaacctc aacctcacaa tcgctaggca ccgggcacgc    16620
cttacgtcct ggatttttcta tccaaccatc gtacagctca tgttgtgggt tcaatactgc    16680
cccgcattta gtacactgtt ttaagtcgct actccacaga accaaacggt agtagtgctc    16740
acattcttcg cgtttagtca ctcggtaaaa gtcggcattc ataagttcga tagtatcccg    16800
tagttcctta accttatcta cctcccggcg taacctgtct ttcagcatgc gtatgtcgcc    16860
gtctttacgg gcgaggtgtt gttgtaagtt atggatgatt tgtttgctgt cagaatcatg    16920
gcctatgtag gcgtcgataa ttgcgttctc ctcgtccgag taccctgagc ggcctgttat    16980
cgaccggtct atgctcatct tgtgtatttc tgctacaacg tcgaacttat tttgcgcgct    17040
gacgtagttg gtcaatcagg tattcaaata cttcgtcttt gctactcatc tccacactcc    17100
tcgcatacga tagctttcag gtccccgtca caaactacat cttctccggc gcaccatata    17160
tacactgcat cttccaggct aatatcctcg tacattcctc ccgcccctct cgtttcgata    17220
cagtaatagt acactattat gtttggttat gccaatacta ttttacgatt aatttatccc    17280
gacgcaccgt aagataacgg ggtttcttcg catgagcacg ccaccactca acacgggcgt    17340
agatgccctg aagcgatgtt actttgccgt gtctgatttc tccgttccgc ccggtccagg    17400
ttacaaggtc atttggtttc attcgttagt ctccgttatc gattcgatga aggtcatgag    17460
ttccttgtaa caagcatccc acctcatagc cgctgcttca ttactcctcg tcgtcgaccc    17520
tgattgtata ggacatatcc gccgatgcat cgtctatacc gtccaccagt tccatcagat    17580
atacagcctg ttgtttagta atcattgttg cgtatcctgc aacaagttgc gttgattgtt    17640
acatttcgtg aaatagaaaa atattaacaa aaatggtacg ctgctactca gcagcgtaag    17700
tcactcagta aaatcctaaa ctactgttac aagcttcctg cggttccgat aacagcgccc    17760
aggtgcggcc ccgccaccac gatacccag gaactatcca cccatcatca tcggcgtccg    17820
gatgcggccc cggggaccac taaaacccta gccataaacg gcaacctcct ttaagacccg    17880
agaatcaccg gcgcggactc tttagaatct tttgccgtgg ggttatttac agggaggtcc    17940
ctgccccatt agagtgcctt tattctcgtc cctcgtcagg taagcgcttg ccgcaaggca    18000
agtgcgttaa tccctgagta gtagactaag aatctttcgg catttcagtt acgttgccgt    18060
tgtccagtgt tgtgccttta ttcttattac ttggtaacta aagggcaggc cttaagcctg    18120
cccactaatc gttacatttt tacgttgcg aatttacggc acatcaagga attcagatac    18180
ttaagagata tgctgccgat gagaatatag ctcgcccagg gcagttcaga tactaaggaa    18240
gggaagttac tgagtttaa gtttgcgggt tcagtaagc cttaacgcgt atccgcttgg    18300
ggcggacccg ctaagctctc acaaggtgaa acagaaactt aagtaacttg aagttacaag    18360
agacaactta caacgaaaaa aatgaaaatg tcaataggtg tgtttatagt tgatttccca    18420
ttatgccgtg ggtatacttg ctttactaac tgagatggag gatttgagaa tgacacagaa    18480
tgaagtagct gagcttattg gggttacccg ccgcacgctg aataactggt taagagacgg    18540
caagttcccg gattgttgtg tccggattat ggtcgccgg atgccgggta cgtttgaccg    18600
ggagaaagtg gaagcgtgga ttagggagaa tgtaaagtga ccgatttcca gaaagggta    18660
```

-continued

```
ttcagaactg tagtcgcgct tacgcgtaaa aaagggtcgt gtagtgttct tgacttgcgc    18720
cgcgcttatt ttcagtacta tagttcctct ctcatcgaga ggtcgctgga agttttggtt    18780
agagacggag cagttaaaag taaggccgga aaatattcgg cagtagctga agttaaaggc    18840
tcccaggcga ccccagaaga ccttgaataa aagaaaagcc ccaacgcgcg aacgtcaggg    18900
ccttaaacac tataaagaaa aagtaaatga aaacaggcca tttaccatac tcatggccgc    18960
gacccactcc ccgtgaggaa cgcgctgaca ttaacgttta caccacgacg tccggcacct    19020
gggatgagtt tgtcgaactt atgcagccgc ttaaacgttc gcgccggaac cccaagacag    19080
accccggcta cattaccgcc gcttgtaccg ccacggtaag ctctaccggt aaagaagccg    19140
ccgaaggtat gttctatcgc tgcaatgcgt ctgttacgtc ttcatccctg gcctatgccg    19200
acgtggacag cgcgacgccg gaagagttcg caaccgactg tgagatggtg cgcgagtcac    19260
gttacgcaat gatgctctac accacggcat cccacaccga agaagcgccg cgctaccgcg    19320
tcgttatgcc tgtacgcact ccggtaaccg gtggcgacat catccgcatc cggtacggcc    19380
tgttggcaca cttccttaaa ggtcgtgacg tggatagcgc cgggttcacc ctgtcgcagc    19440
ctatgtaccg cccgccggta ggaagccagg tcatcgtgtc tgaaagtagc cgcatgatta    19500
cggcgagcaa gcttatggag gaagttcctg aaattaacgt taccggtgct tctgattata    19560
aagttccgga gggtgaacaa tccgaattaa ccgacctgtt tgaagagttc gcttttgaat    19620
tcggcggacg tatgaccgac cgcggcctgc aaatgcccgc cacgccggag cacgccgccc    19680
aatacactac cggcgaacct aagcaggacg acttcctgtt ctgttggccg cgcgacggct    19740
tcgagcgacc caacgttacc ctgtaccacg ataccgacct ggtagctacg ggcgggatga    19800
agcctggcgg acgggatatg tgggcttacg cttgtgcggc caccggctta ccttttgacc    19860
gtgtggaggt ggcgcttggg tgggcggagg gggtcacttg cgacgaagaa gacctggacg    19920
acgaagaacc accagcacca caagcggact tcatcgtcga gggctatatg ccgtctaatt    19980
gcatttggga tatcgtcggt gaatccggga cgtataaatc gttctacaca ctcggcatga    20040
tgtatatcag cgccgccggg tatcggttcg cgggggcaga caccgtaaa gcccatcatt    20100 tctatattga tggtgagggt ggggagttca cgcacacccg tatcgctgcg ttggccgcta    20160
aatacggcga tgaaggtatg cgatatatgc atgtgcttga cgctggtgaa ttcgcggata    20220
cgaagaaact ggtgcgtaaa atgcgccaga tagcgggcag tgaacctgtc gggatggtcg    20280 cttttcgacac tcttaaccag accttcggga actggataga caagttcaat gagaactcag    20340
ccggacagga cggtatgggc cgtgtcgtgg ctatgctcaa agaagtgcgc gacggtacta    20400
aaggcgctgt aggcgttgtc caccacaccc cgaaaggtgg aagtaaggcg cgtggaagtg    20460
gtgcgctgta tgccggtgtc gatgtggaac taacgcttgt ccgcgctacc gagaaacaaa    20520
taaacgttgc gcacaccaag aacaaaaacg gtatgcagca gaaaacaata ggcatggtgc    20580
ttgaaccagt acagtttcgc gaggccccgc cgccgaaaga gttccaggcg gtagaattcg    20640
ctgggggtga gggatacggg gagatagtca acctcgacct tccggagccg cataaagctc    20700
tcgtacttat gccgtggggc ttccagccgt tcgaaacgga cgaggaaaaa gagcgaaacg    20760
aaggattgga tggtaaaggt aaagattccg taaaggatac ggttaaacgg tctaagacg    20820 cttcggcccg tgagtcggtt atgtccgctc tcgaggattt acagcaagcc gatgatacgg    20880
gacgagggtt cacacaacgg caaatagtcg cgagagctgg agaccacagt atcacaaacc    20940
tggtgcttga gaagatgcta cgcgagggtg aattgattct tggttgcgac gaaaacggtg    21000
aagttgtaac gaatacttac aggttgccga tgggtataga cgaccgtaag cgaccgaaga    21060
```

```
accggtatga acctaacgac aacataaaga caacagaagg ggatttagag taaaaagaaa   21120
ggggccatca ggcccctgta tcaccaaagc ttaaccatcg agggtcaaca ccgagagcat   21180
cggcaatgtg gaagatttta aaacagtcta ccttacacac ccggccggtt gccaggtggg   21240
taatcaggct ttgggatacg ccagctttga aagcaagctc agtttgaccc atgccggatt   21300
tctttacggc ggcgctctat gcgagcgcct agctcagatt gctgcatatg tttactcctt   21360
agttagatat gcagtaatag tacagtaata aatacacga cgcaatttac gaaaaagttc   21420
ttgcataaat aatagagtac gattatagtc tttatcacca actaaacagg agaagaaata   21480
atgttagacc aattcttaaa aattacttga acgtttcgta gtcgcccatg aactgattgc   21540
tgcgaatagt gtgaaacaga cgtctaacaa atccgtaagc gaaatgactg ttgacgtctc   21600
cgttgccggt gtcgagacag ttaaaaaaga actggctaaa gcactggaag aagtcgagaa   21660
agcaaaagaa attccggtcg aaggtgagga catcgtcgac actaaaccgg cagaagagga   21720
gaaaccaaaa cgtaagccgc gtaaggcaaa agtagaggaa ccagtacaag aagagaagga   21780
agaaattgat taccaatctc ttcgcgacca gattcaggct atcgacgatg caattaacga   21840
aggccctagt gatgctgcgt gcgatgattc cgatgaactg ctggaagagt tcaccggtaa   21900
gaaaatgaag attgccgcga ttaaagacga agaccttgct gaatacctgg aacgtctgac   21960
agcaatcaag aacaagtatt tcgaagaaga ataactactt aacttatggt gccttcgcgt   22020
aagagggcac ataactgagg gtaaagaaat gatcttagac atcagcatta aatgtgaaaa   22080
cttagcggtt tctactgtac gtggtggctt atacgtagac attaaaaacg cagaattagc   22140
ataaaacgtc ccggtagaag atataggccg tcacgtgtcg cagattaagc gcacgacttt   22200
cgccaagcct tacttttatg tctttgagtc gatgcatgga tgggctatgc attgcgagca   22260
taagacaaga catttaattg accagtggga gaacagagca tgactgataa atggtggctt   22320
aatttgcgca gcggcgacaa agtttacacc gtcggcgacc gcagaaagaa cagcggtgta   22380
gctactgtgc tacaaaacgg caaaaagtac atacacattg cgcatgaagc tcgggcgctc   22440
cgcgtgaata atcgtctgg taggcttgag gattacccga aaacattaat atacaaaagt   22500
gaaaagcatc acatggtcgc tgttgacgca agacgtcagt tcgcgggaat gctgcaacag   22560
ttaagcgact acatcgcga tgattctttc attcccacag aagaacagtt acaggcctta   22620
aacttatatt tggagagttt acgatgattc taaaagaacg cggcggcaat aacgatgttc   22680
acgccttact gtcgccgtca ggtgctaaaa aatggctgtc atgcgctgca tcactggcct   22740
gtgaaaaaga tattcctaac acgtcaggta agctgcggt attaggcaca gctatgcaca   22800
ccatagcgga gatgcacctt aacgcctata tacgcggcac tgcactgccg ttagaacgtg   22860
aagtcggcgc ttatgttctg gatgaaggta aaggccagat taaggcgcta atcagcccga   22920
tgaaaggcgc ggtactgatt acggcgggca tgattgagca agtgcgcaag tacaccgact   22980
actgcaaacc gattattgat gtagcgactt acgccaagct ggaaatgcgc gtcaatctta   23040
ctgaggtatt gcatccaggg tacatccata gccctgacgg acggcaagaa gaactacaga   23100
cattcggaac ggctgacctt gtcgccattc aggaactggc taacaccaac gagcacatgc   23160
tcattattgg cgacctgaaa acaggacggc atcgtgtcga agcgaagaa acaaacagc    23220
ttatgcttta cgctcttggt gtttatcgcc gactcaagag acgttatagc ataacaactg   23280
ttcgtctggt catattccag ccgtatgctg cggcgcgtc ggaatgggac atttcggttg    23340
aaggtctgga actgttcgct aagttcgcgc agaaacgcgc ggtagctgcg cttgacgcgt   23400
```

```
atcggcgtgg taagaaaaac cttaaaccat cagacttcaa gccgtcggtc gacggctgtc   23460
agtggtgtcg gttctccgaa cagtgcgccg cgcgtacaaa aaccgttaac tctgtactgg   23520
cggaagaact ggaggacgac tttgcgctgg aacttacacc cggagcaact cgtagctgag   23580
tatgagaagt tgccactgct gcgccagcac atcgacaagg tcgagaaagc gatggctgcc   23640
gcgttgcatt ccggtaagaa agtgccgggg tacaagctgg ttgaaggccg cccgggtaat   23700
cgtgcgtgga aagataccga tgcgctgctg gaaacgctat cacattttga gttgggcgct   23760
gaaatgcttc ataaagaagt actaatgacc ccgaccgagg ccgagaagca gcacaaaggt   23820
tctgagctat gggcggcgct ggagaaacac gtaacccgta agccaggagc gccgtgtgtg   23880
acaacggtcg aagacaaacg gccagaatgg aaaaatgtta ctgaagacga tttagaggcc   23940
ttgacatctt aatcgtactc tattatatta ctaatcactg accgggcagc tccccggata   24000
aactctaaaa cgcgagaaaa ctaaaatggg aattaaactt aatcttcgta aagtacaaac   24060
cgcatggctg aacgtattcg aacgcgctaa agaccgtgaa ataatgacg gttccgttac    24120 taaaggtacg tataacggta cttttatcct gactccggaa cacccacaaa ttgaagagct   24180
tcgcgatacg gtattcgcag tagtgtcgga agcattggga gaggccgccg ctgagaaatg   24240
gatgaagcag aacttacggc gaaggtaagc acatggacaa gtgcgctgtg cgcgacatcg   24300
ctgagcgcga taatccgttc gaagacttcc cggaaggttt ttacttccag gccaagaaca   24360
agcaacaacc attaatcctg acttcggtta agggtgaaaa gcaggtagaa cctgacttca   24420
atattgatgg tgagcagatt gaaggtgagc aggtatatag cggttgtgtg gctaatatct   24480
caatcgaaat ctggttctcc gagcaatata agttttagg cgcaaaacta acggcatca    24540 aatttgccgg tgaagggaag gcattcggtg gttccgcggt ttctgccagt gtcgacgacc   24600
tggaagatga tgaagacgaa acaccgcgtc gcgaacgccg ccgtaaccgt taatatattt   24660
tcttttcaat taaggcggct tcggtcgcct tttctataag ggtcaaataa atgaatctgc   24720
tttatctcga tactgaaaca ttttcagaag ccgatttaaa aaaagtcggt tcctatgctt   24780
acgccgaaca tccgactacc gaaattgtta tctgcaccta cgctttcgat gaaggccctg   24840
tgcaagtatg gacgccacc gacggcagcg atatgccgcg tgatttgcgt cgggcgatgc    24900
taaagctgca aaaaccagac agcaatctca aactggtagg ccaaaacttc cttatgttcg   24960
accgaccagt tattaagcat tgctggggat tcgaactcct ggtagaaaac attatagaca   25020
ctatgatagt cgcgttccga catgccctcc cgggttcact ggccgcgctg tgtgaggttt   25080
taaacattga cgcaagcatg gctaaggata aacgtggtaa ggcgctgata cagcgattca   25140
gtaagcctac gcccaagaac tataagattc gacgttatac tgccgatacc cacccaaaag   25200
agtgggcaga atttattgca tacgcaaaaa gcgacattac gtccatgcgt gaagtgtata   25260
agaaaatgcc taagtggggg aattctgagt tcgaagaccg cgtgctgcac ttagaccagg   25320
tgattaatga ccgaggattt aaggttgatg tggcattggc ggaagcagcg attgaagcag   25380
tcacgcgcca taaagaagag ttacaggaag aagcccaacg taaatatggc ggttcactaa   25440
ccggcaaaga cttcttgcct attttacagg agctagcgcc agcgcaccgc atacacaacg   25500
cacagaagtc aacactaaac gatttgctgg cggatgagga tttaccggac gacgcccgca   25560
ctattatcga gatgcgtctc ggggctgctt ctaccgcatc gacgaaatac gcgccgttgc   25620
tgttaggccg ttcttcagat gaccgccgcc gtggttgcct gcaatacgga ggagcgaagc   25680
gaacattgcg gtgggcgggg aaaggttttc agccgcaaaa cctggcgcgc gggtattatc   25740
acgacgatga actggatagg ggtattgccg cgttacttaa aggccgtgca caccgccgtt   25800
```

```
ttgatgtggc caagctaaca gcgtctaccg tccgaagctg cattatcccg gaagccgggc   25860
gtaagtttgt tgttgcggat tactctaacg tcgaaggccg tgggcttgca tggctggcgg   25920
gcgaagaaac cgcgcttgat acgttccgcg ccgggctgga tatttactgc gtaaccgcag   25980
gtaagatgtt tggcatggac cccgacgata tcaagaaaga acgtaaagac ttacgccaga   26040
taggtaaggc ttgccttcac cgtcataccc aagttttgac cgattggtgg atttaaggat   26100
attatggcgg ttcatcagc atataaagta tggaatggcg aaaaatgggt gaatacaaaa    26160
ggcacgcacc ttatggggtg gaaaccggta ataaatgtgg acggggttct aatgaccgaa   26220
gaccacaaaa tcttgacgca ttcctggaag gcggcaaagc aactcgtttc aaacaaatat   26280
atgatgggcc tcgccctggg gagaggtggg gacgcctggt tatcctacgt gagctaccaa   26340
aacgacaagg ccaaagacca actactcgtc caatgtgatt gcggagagat gccggggcgg   26400
gtctattatg acaatgtccg agcgggtaaa accactcaat gcaacatctg cgcccttgaa   26460
gcaacaaaaa aatatcgtaa aaaatatttc tgctacgaag acgcaatgcc ggatgatgcg   26520
cacagaacgc gattgctcaa ccggttgtcc gcggcaatcg tgcggacaac aagccccgga   26580
aacaagagtt acaaaaacta tggggctagg ggtatcacgg tatttgacca gtggagggcc   26640
gataaaaggt cgtttcttag atatgttcaa actttggaag gctgggatga cccaaacctc   26700
gaaatggacc gaatcgacac agacggtaac tacgagcctg gcaacattcg gtttgtcagc   26760
cgttctgaaa actgccgtaa cagacgtcga atacctgagc ttcaacgaaa gtatgatgca   26820
gccgttgccc gcattgctga gcttgaacgg gaaattaacc tactgcgagc cagtttacga   26880
cctgattgat gtggaagacg gcaaccgttt tcttatagcc tcagactcgg gctttcttgt   26940
ggcgcataac tgcgaactgg gcctcggcta cgagggaggt gtcggagcgt tcgttacgtt   27000
tgctaaaaac ctgggtcttg accttattga gatggcaaaa acaatggacg ggactttccc   27060
cgaccacatc tgggctgcta ctgcacgtgg gtatgagtgg gcgcgtatcc aggaagccaa   27120
gagaccaccg catcccggtg aaaaggatga caggccgtcg tatatacttg acaagaaagt   27180
atggcgcaca tgtgacgcga tcaagcgtat gtggcgtgag tcacaccctg aaacagtagc   27240
gttctggcgc gaccttaaag acggaatttt agccgctgtt cgtaatcctg gtcgtgaatt   27300
ttgggctggg gcacacttgc gccggaatgg tgaaagggct atccgcatat ggcgtaccgt   27360
agaatttgat tcgtcgggca ggaaggttcc tggctggtgg ttgtgtatgg agttgccgtc   27420
aggccgtatc ctatcgtatc cgggaatcgg cgttagtgtg acaaaggaaa cagacgaaga   27480
cggacggata aacaccaatg taagaattaa gtaccagggt gagaaccagt taacacggca   27540
atggaccacc ctgtacacac acggcggaga aggcttgtga aaacattgtt caggcgttgt   27600
gccgtgactt attggcctat gcgatgctta atgtagaagc cggtgggtat ccaatagttc   27660
tttctgttca cgatgaactg gtatgcgaga ctccggatac atcagattac acggtagctg   27720
aactggaaaa actaatgtgt gcattgccag aatgggctga tggttttcct cttgtagcgg   27780
aaggtgcgga gttaaaacgg tatgctaagt aaactgatta tttattattt cagggaagaa   27840
gactgtcgaa tctgtccgcg ctgtgggggtt aagcacacga aacgtgaggg gtgcaataga   27900
tgagtacgcc tgagggccgc gtccagaaat atgcaaaaga gcgattcgag ccctggggg    27960
gcctcgtacg caaattgtcg tacgaaaata gagtgggcgc tcctgacctg ctggtgattc   28020
tccccggtgg catcatctgg ttcgtcgagg tgaagaaaga cgaaaacacg aagccagacc   28080
cgcaccagtt gcgcgagcac gagaggatgc gtaaacgcgg cgcaaatgtt tttgttgttg   28140
```

```
ggtcgaagaa acaggttgat aaattaatag aacactatta tatttagtta acaccaaaca  28200
gaaataaggg aattgagaaa tgaaatatga atatgaccgc aaaccagcac gtgacatcgt  28260
accaggcgat atgattttca acgttaaaac ccgccagccg gttgccgttg atactgtgtt  28320
cgtcgagtca aacggtaaac tggttatcga agatgtaact ggcaatgtta cagcgttcgg  28380
gcgtaaagag ctggtgctgg tgctgaaatg agtaaattca atagaagacc cgatattgag  28440
aaggcgaaac gtcttcttaa ctatgaccee gaaacaggta tatttacacg aaaagtaagc  28500
ataaaaggga gaaatgcggg ggaggtagcc ggagggccga acgacaaagg atacatagtt  28560
attacagtct ccggtgtaag aataaaagcc caccatctgg catgggcttt cgtctacggg  28620
gaataccaca atggtgagct tgaccataaa gaccgtaaca gggccaataa cgccataaat  28680
aatataaggc ccgcaacaag gagccagcag attcagaacc gcgactgctc atcgcataac  28740
actagcggcg cgatagggt ttaccaaata ccatctggca ggtggcggcg ccagaatagg  28800
cgtcaataac aaatacatcc accttggcta ttttgacact atagaggaag cgtcgcgcgt  28860
ataccaaaga gctgcggaaa tatacttcgg ggagttcaag gcatgagtaa gtttaggcgc  28920
agggaatacc agaaaataat gacgtcgttt atgctacagc acccacgttg caatatatgg  28980
tgcggtatgg gtggcggcaa gacctcgtcg acaatgtggg tgcttagccg cctgttccgt  29040
aatgggcaac ttaatgacga cgaccgagtg ttaattctgg cccctttacg tgttgcgtca  29100
ggtacgtggc cagcagaaca agagaaatgg aacttcccgt gtctgagtgt agtagatgca  29160
actggttctg agaagcgacg catcgcggcg ctggagtcag acgctaacgt ggtttgcaca  29220
aattacgaag ttatagaatg gcttattgac tactacggca aagacgactg gccttttacc  29280
gttatcgttg ccgatgagag cacgaaactg aaatctttcc gcagccgttc aggcggtagc  29340
aagcgggcaa aggcgcttag taaggtggcg ttcggtaaag ttaagcgttt cattaacctg  29400
accggtacac catcaccaaa cggcctcaaa gacttgtggg gtcagaactg gttcatcgac  29460
gcgggtgaac gccttgggtc ttcatacacg gcctttaccg atagatggtt taactcggta  29520
cagaaaggca aatctgcgat ggcgcgggag taccatgctc gcccaggcgc ggataacgag  29580
attcaccaga agatgaagga tatcagcctt accattgatg ccgccgagtg gttcggttgt  29640
gaagcaccgg ttattgtacc ggttgagatt gacctgccga agaaagcgcg tcaagcctac  29700
atcgatatgg aggagaagtt attcgcggaa ctggagagcg gagaagttga agcggctaac  29760
gccgccgcta aaacggctaa gtgcttgcag attgcttccg gtgccgtgta tgtgtcgggg  29820
ccggatggta agcaacgaa agactgggag aaagtgcacg acgcgaaact cgatgcgtta  29880
gagtccattg tcgaggagtt gcagggtgcg ccgctgctgg tggcctatca gttcaagcac  29940
gaacttgagc gcattcttag gcgattcccc caggcgcagg cgtttgcgaa aggtgctaag  30000
ggtaataagc agatggaatc ttggaaccgc ggggaaatcg agattttgtg cgtgcaccct  30060
gcatcggcgg gccatggttt gaatttacag gacggcgggc atcatctggc gtttatttcg  30120
caaggctgga acctggagca ctatttgcag gttgtcgagc gtataggtcc tgtacgccag  30180
aaacaggctg gccacgagcg tccagtgttc ctgtatcaca tagtcgctaa agacacgctg  30240
gatgaggtcg ttgccgcgcg tacgacgag aaaaaatctg tccaggaaga gttgcttaat  30300
tatatgaaga gacgaggtaa gagatgaata atgagtttga tatcgacgct tgcaacgaat  30360
tgataaaaga cgccattaat tcccgcgagc aacttctagc tatgcaatta aagcgagaaa  30420
taaaacgtat cagggaactc gaagaagagg ttttacggct acggcagcaa agagacgctg  30480
ctaacgcgca acttgactgg ctactagaac aacaggaagt tgacaaagag aggggcgcta  30540
```

```
aatgaaatac tcaattggtg cgaaatgctt tttaataggc tacgattgg  ctgcggtcgc   30600 tttacttatc gctgctgtgg ttctgttatc ataaattaag gccccttacg ggcctttac    30660 tatttatgcc aaagttaatc ttgtatagct tccatcggcc cgcttaacta acgctttaag   30720
gctatcgccc tccagataca gtgatataga cccgttatcc ctgacagcgt tgtctggtag   30780
ggcggacatc gctaccggta tctcaacagc acgataatcg cccctattta ttttttaatga  30840 cacggcatcg ggcaagctgc ccgaaatagc tgtgacttct gtccacgctg aaccagaacc   30900
tgggccgccg tttatgtggg agtacacgga accactatca agggtctttg acagtttatg   30960
tatccgtaac cgaagcgccg cagaatcatt attgaaactg tttatgcgag agttaccaag   31020
accttcctcc atcaaattgg ctacgttaat ccttgagggg tctacgaagc cggttatacc   31080
acttaccgtg gagttaggcg cgtctatcgt caacccctgt ccactagtgg agcgtatgcc   31140
taccaaacga agaccgttca cacggcaggc cccggagatg tagatctgat tcgctggaaa   31200
atctttagta tttgtgtcga ttatagcaat attagtgaat accgtttcgt gagtaagaag   31260
atatgcaccc gaaccagcgc aatcctcgac ggttatgtta gagacataca gacctttccc   31320
atccatgccg aaacctacgc ccaaagaacc cctaaccagt agattgtcga tcaaatggtt   31380 taggggagc atatgtaccg ggtattgaga atacgggaaa tccccgggc ggtcatcttc     31440 tgggttcatg tcggtatctg cgcctaaatc gaagccgtcc catacagggt atagcaccgc   31500
cgaatcccgg aattgcaggt tgtagttacg agaggtcgta gaacctaccg tgccttgcca   31560
tgttttaaca ccactttcgc cggcgcgata cgaggtaaac ccgatgaccc cgccatcgcg   31620
cgcgaaaccg ccattgtttc gtaagaattg agcgctactt accgaaccgt aacttgtgcg   31680
cccgccaata acatagttac ccttgcccca atcgccgctc aggttttcaa aggtaattac   31740
gccatctttt ccgccgctcg ggttgtcagc gtctaccatc ttacagaaat ggcatccgcg   31800
gaacaggaaa cacgccataa gaccactcgc ccggtgaacc tcgacgcctg tacattcccg   31860
aatttccagg gtagaagata tgctttgccc tttagcttcc ggagggagaa gggattctat   31920
accaggaaac ttggcgtaat cgtttaccgt cggctggtat ccatctgttt tagactgttt   31980
aagtgtggcc acgattgccg cggggtcggt tatccactga ttatcgtcgg tccacggttt   32040
taatcaccca cggcgttgta gcactctcca taaagggggc tattacaatg gaacctttac   32100
ctaattgcgt aaataccagg tttccgtcgc cgataaactt cgctttacag tcgatggtca   32160
gggtcttccc gctgaagtta acggtctcgt tattactgaa agtgtaatcg cggtcgataa   32220
gaacgctatc aacggcggca tccgccaatt gttgtaacgt agtaaagtcg acagcttaa    32280 cggagtattt aaatttctta tccgcttccg cgcgaaaggt aatatctccg aacgcgaccc   32340
aagcggaatc cgaaatgccg cctgtcgtaa gaggtgtcga cgccgcaggg ataactttcg   32400
gcagggggcc acgccatgcg taatagttac cgtccccgcc atcttctttc ggccaaagaa   32460
ccgctttatc cgcgtcgttt acgccgagag taccccggt cgtaaagtta aaagatgccg     32520
gggagaaacc agcatcacgt aagactgcgg gaagcgtctt ctgcgtctgc ccggttacct   32580
ggttagtggc gtagtcgata tccgcaccac cagctacacc gccttgttta ccggtgatca   32640
cctcggcttc gaaaatctgg tgttttttag ctatttgtaa atcattaagt gacaatacat   32700
caccgcaacc gctggacata tggctatcct cttagttaaa accgttatcg aatccgctgg   32760
agaacgcacg accgaaagga ggcacgttgt caaacttata gaaatccttg tcatagttaa   32820
acccggttat tttgactgtt ctgtcatcgc cagggtctac cgtagaaaca agaatcatct   32880
```

```
gagcattatg ccttgcttcg ttgccgaatg aaaattcagt tttcaaagcg ctattaccag    32940
tgtaaatggc ttcttgcggc acagacgtca taattacttg tcggtcatgt gcgccaggga    33000
caacacgaac actttggact ccgccatcac gtaacttcag aaccaaataa tggtcatctc    33060
cggatgtgaa cttaaccggc tgggatagct ctacggtaag accgttaacc gcggttacgt    33120
agccgtcgta agtagacata cgcgaaccct taaccacact aacggcacga ttcggaaggg    33180
caaaaatacc ctcttcagtg gcggtaaacg acaccgaaat tttctttaaa atgttcttct    33240
ggtggcgacg gtttgccgcc cagaaagcct gcttatagtt gcggattcct tttgagtcgt    33300
aagtctccgt tttaaggccc ccggtttcgg gtatggttat agtctctttg acgttcgtct    33360
tagggtctat gtacgagaat ttaaggctgt caaaaacctg agaatcgtta aatgttctgg    33420
tccacttttc agaagtaccg gccttgcttc ggtgggtgaa caccatctcg ggcccatgc     33480
gagggcgctc aaaatcgaga aggatatccg ccccacgccg atatggggtg cagaatatgg    33540
cgtctgctat agtactaact atgtcctgca tggtggtttt atagtcatca aacgtgtagc    33600
aaaattcccc cgcctgtttg tcaccgaaat acgcttcgac ctcgttctgc acggcaagta    33660
acttatccat gttgcgtacc gtcaggttta aaccacccac gtccgggtca cgtgccaggc    33720
ggatgagaga ttgcacggcc tgggtattgg gagtcatcgt atcctcaaaa acgccattac    33780
caaggtatt gtataccatt tcagtagcaa tcatacgcaa ctgcggttgc ttaacttctg     33840
cagcacgcgt tgtctgcttg cgcatcgagt gtacagtagt tctgttgccg tagtgcggag    33900
tgttatcgcg tgtttgcccg tacaagttaa cgtacgttat ctcatcaact acagacccct    33960
cgaaattaaa gtcgaggtct gtcacccttc tggcgcgcac ccgcaccctc gacacaaccg    34020
gcaggtcggc gtaaatagtg acaccgttgt agtctggggt tcgcccggac acggttcctt    34080
gtgcagtgta tatcggccca taaggggtgc tattttcatc aagcagctgg tactgtatct    34140
ccgcggtaac cgacgctagt gttttagatt tgccgttgtc tttatacata ccattggcgg    34200
cggcgatatt ggcaactatg cgctcaacct cggtacggtt tattgacacc caatcggtta    34260
aggttttctc gtatgtgtta tccggttgca gcgacgcctc tccgtcacct cgaaaaaatg    34320
aacctggtct tatttcttgc caccgaccga taaggccgcc aggtacaata aatgtaattg    34380
tcccttcgga tacgcttaac acttggtacc cacccccgga aaggtcaaca tctgtatttg    34440
tccacgctga caccaacgaa aacgtgtcat taggcaccaa cactccagaa aaatccgaac    34500
cacctgttgg gtcatatatt gtgccaatgt tcccggacaa agacgggtac ccggacatgt    34560
aagagaaaga aatacccagg ccgttgggag ctttaagaac cacgccatct acttcgttag    34620
attctacggt aatgtacagg ccctgctcta tagggtcgcc gaccatgacc tggggtgccg    34680
atgtgttatt gggcgatgta tatggtgagt acacggcaac cgacgtgcct gttatgtctg    34740
atacgcgggt gtccccgtca gttataccct cagggtgtat gtctaggtaa ccacgcccgg    34800
cgtcgtaata gccgtactct acaattttac cagcggcgtt aaacaccta taagtagaca     34860
taaggttatt tgggatagtt tgcaccgttc cgcagatgtc gtagctgcgc tcgtatgggc    34920
gggccttgtt gttacggtcg gtgagactgt tgttcgggga atccgcctgc gagttcgcaa    34980
ggttagattg acgccccttt cactgatggt gataatagtt tcgctagcgg tttaaggata    35040
acgctaaaaa tcttcattac gcctttaatg gcaccaccac cggcagattc cacaatgtgg    35100
aaagtcgcgt tttctttcag tgcttcgaag tcttctgtta cgtcgttatc ttctccgatt    35160
tcgtcaatga aaacacgcac cggcacccog tccggaacat ggttcacgac gaagttcatc    35220
ggattatcgc gataacgttt aacgtcaaac gtgccgtctt cgttgcgggt atagtggatt    35280
```

```
actagcgcca aaattcaatc tccgaataag tatctttaag gtcttccaga ctatccagtc    35340
taacctgtct ggacgccagc tcacagtggc ttaccattcc ttcgtaatat accccagcat    35400
gccacactat tcgcccccta tgtttcactc ctagtagaac cgcgtcaaaa ttctgcggtg    35460
tgaccgctcg taccagacct ttcggattag agtggccatc gtcgaaggcg cgcctattg     35520 ccgttgggct tgttacatcg aacatcggtg tcgataaccc cgcgtccgcg cgaacgttgc    35580
ggacgtgatg ccagcaatta cggcggcgaa agtcatacgg caagccagtg taatcattaa    35640
tattcacgat gtcagtatcc cgcgaagtaa gggaatctct tccggtgtca tcagaatccc    35700
tgttgcccgt tggttaagca tcggcgtacc ggtttccgct gtgaatacgc ccttttcttg    35760
cgtgagtgtt tgtaactcgt acaccaccgg accgtcgcat gggtatgtca ggtcggtact    35820
tacataacgg cggaagatga atttaggtaa ctccttatta tcataggga tgcggtccat     35880 ttcctcgtct agtatgttaa gcacatccgg cagcgaaaag gatgcggtct ggtccatatc    35940
gttattgttg ccgcgttct tggcctccat tggcgtacct tcgaatgtca cgacctcccc     36000
ggtctcaaga gtagctgtta aatcgtcagc cccgcgcaca agtaaccacc gtttcgagag    36060
aagtggatgg tatatctcaa gagttataaa gtccatctca ccatcgggat tagacgctag    36120
tttacgtcgg tatgctgctt ctactgattc ctgactcatt gcatagggtc ccagattcgg    36180
gggaatgtag tctgatacac tccgtatgtt ttaagaaatt cgcccaggca atcaccatag    36240
cacccgtaca aatcgggtag gttctggttc aggcaagcat tgttggtttc ctggaatggt    36300
gatttctcgg cggtggccgt gaaggtgatt acccaattct ttccgtcatc tgtggactcg    36360
ttccacgtgg atgttaacgt tacctggtaa tcctcaatac cctgacccaa gtcgtgcttc    36420
atccagaaac tggacgcacc accgtctacc ttttccatga aactgaggaa tgcctgccgc    36480
cccaacggcg atacgaccag ggtaacgtta atcggaaaca cgtcaaaata ggtgtcgcgt    36540
ccctggcgaa ccccgccacc ggccaggtct acccgccaca cgttgttacc gcgggtcatc    36600
gagtagcctt tcgatactat aggcctcaaa gaggccggga aatggtaatc gctcatatca    36660
atatcctggt tggccgcgtg tagcgcgacg tgacttagaa atggcgctgt tactatcttg    36720
taacgctgaa cttacggttt cactgattat aatacgtaaa cgaccttcgt catcgcgttc    36780
tgttgcagcc gaatcaattc ttccagtggt gttgttcacg atagtaacat tatctccacc    36840
ggatttagcg ccattctcgc ccataatctg tcgcatctgc tccgccgttc ggacacggga    36900
ggcgttggca ggcataatca cttctggttt accgcgttcg gcaatagtag acatctggcc    36960
tgcggccagg ttgccgccct gctcgcgcgc ggagcgaatc ttacccacgt tggcgagacc    37020
tgcggctacg gcagcagcag cagcaactgg cgctaaaaat ggccctacta ctgggatggc    37080
cgccgttgat ttatacgctt ctactgctga cgtgtacgta gcgattgtcg cctgtgcgat    37140
ggcaaatgct ttatatgccg ttgatgcttc ccctaacgcg gaccctatgt tgctcgccat    37200
attgccgaaa gccgcgccgg tcgccttcgc tcggtcaagg gagtaagatt catccatggc    37260
gcttaacgtt tgttggtaag tttcttcggc aatcaaaccc tgcgcatgaa aatcgttaag    37320
tttttgtagc ttgacctcgt actgccggtc taattccgca aattctcctt cagcaagggc    37380
ctgcatctga gcgacatacg catccgcgga gaactgtttt tccaggcgct ctttctcgcg    37440
tttatctaac tcagcctggc gggccgtatc cgcctcgagc ataatctgcg tcttagcggt    37500
ttcgtattgc tggtcactaa ggagacggtt gctgtagaac tcctgtagct tagtaagttg    37560
ctcttcttgg ttagcttgta tcttctggaa tacgtcgtcg ttaaggtgga ttgactgata    37620
```

```
atagaaatcc tcagcggctt tcttctgacg ttcgaatgcg tcgacggatt tcttagcagc   37680
attgtccgcg gaatcgccta cagaaccgtt gtctttaccc gacactttaa acttaccaag   37740
accctcggcc ttggccgctt ctttatcgat gtcgtaagcc gcgcgcttca atgcgataag   37800
gtcttcctga gcttctacct gttcacgaaa acttttacgt gtcaggtcag tcacagctct   37860
ttgggtatcc atagcaagcg ctaactggaa gttaaggttc ttggcctcga ccaccgactc   37920 accggggtc agcgccgcct ttaccagacg accggcgtct tgtgcgccct taaccatatc    37980
ttcaaaaaac cgctccatcg ccgtgaattc ctgggcgata aagtccaggg cgtccgccgc   38040
ggattcggct atcgtagaag cggttttcttc tccgctcccg gtgatgcttt cgctggtata  38100
gttccaagcg gagtttaaag cgtttagggc gtctccaacc atcccgaagg cggcgtcgaa   38160
tgaggcctct atagcacctc cgacttcgga cgccatatca ccccacatct tcatctcagc   38220
gacaaactca cctgacgcta cccgagaatt tatctcctgt atcaggtcat caacatagcg   38280
taaaggttcc gccagtgacc ctacatctat actagtggca agggtcatct tcaactgaga   38340
ccatgagtct tctgcgctag caatagcgcc attgagcgtg ttcgcctggt ctgccatagc   38400
gcccgcgaag ttcacgttac ctatgttaag aagatactgc tcgatatcgg cggcattttt   38460
cttaactaca gtggttgttc cctggaaggt gaattcgata tccttttggt tctgcttggc   38520
cttgataccg aattctttca gacgttcgaa ttcaaatgta ctcgcatccg ccaccgcttc   38580
aatcatctgg ctaaggtctt tacccatcgc cgacgcggta ttgccgtaag agcggagcgc   38640
ttcttccgat ggagttaggc ctagagctac cagcttacgg aatccttcga ccgcttgctc   38700
aagtccgtaa ggggtgtcgc gggcgaagtc ctgtaagata ctcagggcct gctttgcgcc   38760
ttgcgtgctt cctgttagtg ttttcaggct ggcggacatc ttgtcgagtt gccgttgtga   38820
ctcgactagt tcctgcgccg ccttataggc tgtagcggct acaacggcgg ccaggccggt   38880
gacagcggcg cccgcaactt tgcggatttt agagaggtta tcaagacggt ctgatgtggc   38940
cttcgcgcct tgttcggtta cctttactac taagctagct acatcagcca tcgtttctac   39000
cctcaaaaat ggcgtctaag cccatgataa tttcagattc aaacatccct atattctgac   39060
ctgaaatagc gctatacgcc actaaatctg accaactaag ttgctctctt gggtatagct   39120
ttacgccgtc gtcatcaacg cggcgggtga atttaacatc acgatacttc tcaaaagtgg   39180
tgagtagttc aggggggcat tcaggcccgg cgtcctgcgt tgtttcttcc gcgtcttcta   39240 ttaccccat agcgataagc gcggctttgt gcccgtcggc tatactgtca aacttgcgcc    39300
tttcgtggcg ggttatgaag ttccaacggg cgaactgaaa caacgcgtct acttttcctg   39360
caattggcgc aactgctcat ggtggaatac gactacatgt tctgccaggc gcttatattg   39420
ggcgagaaga gtctcaagat tttccttagt gaactcgtca tcaagactcc agccattcac   39480
caatttcgag ggccaattgc cggtttaggt ctcccgccgc gtcttccatt tttaaattgt   39540
attctgagaa gtcttttttgc tcttcgcatt tatcccgaag cggttttaat ttacctaccg   39600
ccgctcggta cgccagggtg aaggcccgca tagctttaac cgcaacatca gcctcaggag   39660
agacaacgtt caaccattcc cctgaatctg taccatcttt taaggaatc ggcatacgcg    39720 cgccttttct cggcttctgc ttcgtagtaa aaatcgctaa gtttcatagt aatacccttt   39780
ggttagtcgg ttactggttg gtagttgcgc caggcgggaa ccacccgctt ttccggtgcg   39840
accgtaggcg ccaaataaga ataacaaaat agcttgcata accgttaata gtggcctatt   39900
atccttacgt caactaaaca atatgaggtt aagaacatga ggcgtttcta tcggtgttat   39960
cgcgtttatc tatttcatcc cgttcctggt agccttactg cgtaatcata aagctaaatt   40020
```

```
aggaatcttt gtatgcaatc ttctacttgg gtggattctt ctgccgtggg taggcgctct    40080
catctgggcc tgtaactcta acgttaatgg taaataatct ggcttaatta aaattacatt    40140
attagaatca gatttgtctt aaacaatcag gggaaataag catggtcact cgcaaaataa    40200
cagatgaaca gttgcagcaa gagctaaacg ctggtctcgg cccgaccgaa atagccaaaa    40260
agtacaacat gtcccgccgt aatgttcagc ttagttctgc gcgtctggca agaaaggag    40320
ttggtcacgg gcgtgacgta agccacctgg tgccggatgg gtataagatt aagggtacgt    40380
cgtcactggt ggatgagttc ggcaatacga aacttcagtg ggttaagact gacgccgacg    40440
ccgagcgtca ggtcgagttg atgcgagccg taatagatgg gatgaagtcc gatattacgc    40500
cagtttcttc ggtccctcgg cctaaaaagc gactaaacga aaagttgcta atctttaca    40560
cggtttctga cttccattta ggtatgttgg cctgggcgga tgagagtggc gacgactggg    40620
atatgaagat tgcagaagac ctgttctcga gatggttcga cgcggcgttt caaaagcgct    40680
gatgcggtgt gggtgttatt aacctattag gggactttgc gcattttgac agccttgatg    40740
ccgttacgcc tgccagtggc catgtactgg acgcggacac gcgttaccag aaactggtgc    40800
gctacatgat tcgtatggtc aggcgcgtgg ttaatatggc gcttgttaag cataaaaatg    40860
ttcatctcct aattgtgcaa ggaaaccatg acgagtcagg catgatttgg ttggctgaaa    40920
tgtttaacac tctttacgat aatgaacctc gtgtttttgt agatacatcg gctgatgtct    40980
acaagatggt ccaacacggt aagacgaccc ttttctttca ccatgggcat aaggcgagat    41040
tcgatgctat cgaaccggtt atgatcgcca agttccgtaa ggcgttcgga gagagcgttt    41100
acagttacgc ccatgtgggc caccttcacc atcagaagat tgtggaaagc cgtaacatga    41160
ttgttgaaca acaccgcact ctcgcggcga aagatgctta cgcatcacgt ggtggatgga    41220
tgtcaggccg cagcgcgaat gttattactt acagtgccga atacggcgaa gtcgcgcgtt    41280
taactatttc accggagatg ctgggatgac taacaaatac aatcgcacaa tgacaaatac    41340
tgacggagat agcattacct gtgatgtgta cgacgttctg agggcatttg atatccgcga    41400
cccagcgcta cagcatgcgt tgaagaaact gttgtgcatg ggcttgcggg ggcacaagga    41460
cacaggaacc gacttagcag aagcaattga agtctggag aagttacgga ataccgtag    41520
taatattgat gagtgaggca tgatttggtt ggctgaaatg tttaacactc tttacgataa    41580
tgaacctcgt gttttgtag atacatcggc tgatgtctac aagatggtcc aacacggtaa    41640
gacgacccct ttcctttccac atgggcataa ggcgagattc gatgctatcg aaccggttat    41700
gatcgccaag ttccgtaagg cgttcggaga gagcgttac agttacgccc atgtgggtca    41760
ccttcaccat cagaagattg tggaaagccg taacatgatt gttgaacaac accgcactct    41820
cgcggcgaaa gatgcttacg catcacgtgg tggatggatg tcaggccgca gcgcgaatgt    41880
tattacttac agtgccgaat acggcgaagt cgcgcgttta actatttcac cggagatgct    41940
gggatgacta caaatacaa tcgcacaatg acaaatactg acggagatag tattacctgt    42000
gatgtgtacg acgttctgag ggcatttgac atccgcgacc cggcgctaca gcatgcgttg    42060
aagaaactgt tgtgcatggg cttgcggggg cacaaggaca caggaaccga cttagcagaa    42120
gcaattgaaa gtctggagaa gttacggaaa taccgtagta atattgatga gtgagaaaaa    42180
ggcccctttc ggggcctttt ttttatcgtc acaataaaga atctgatttg aacgataagc    42240
atgttcgaag ttaaatataa ccataccaac aagaggagat gaaaccatga acgaattaat    42300
gaatgttagt gaagcacaaa ccatgtccag ccgtgagatt gcggaactga caggtaagga    42360
```

```
gcataaaaat gttctggctg atatccgcaa aatgttgtct gagattcaat cggctgaaaa    42420
gtcagccgat tacaaagaca gcaaggggcg cacgtataaa atgcttcttt tggataaaga    42480
ggaaacgtta attctgattt cagggtacag catcaaaatg cgcgctgcca tcatccgccg    42540
ttggcaggaa ctggagtcac aagcgagcaa accatcctta ccggtgccca agacaatggg    42600
ggaggcttta aggttggctg cggacttgtg ggaggagaaa gaacgccttg cgcttgagaa    42660
caaggaaatg gcaccaaaag ctgatgtcta cgaccgcatc atcgacagaa ataacttgta    42720
caacgcgacg caggtggctc agaagttcgg ccaatctgcc gtgtggatga ataaacaact    42780
tgaacaattt ggcgtataca atcgctccgt aaaacgcggt cgtgtcttcc agcaatggtt    42840
tgtggataaa ggctacggca tcatgaggga acagaaact  gggcattcac aggctatgtt    42900
cttcgctgaa ggagagatgt gggttattgg taagttaacc gaagaaggct tgatttaaaa    42960
ctaaggcccc tttcggggcc tttttcttag gcgtacttaa tgcgctgaat aacaattgaa    43020
gactggaact ggttaccggt tgcctgtccc tcaagagaaa gggtaataga ctcagggccg    43080
ccgatttcag gagttgcgga cgtcagtgaa gcacgcttga gtgtaaagct catagcgcca    43140
tccggaccat caagaaccga agatacctcc atttctgttt cattccagga atttattcaa    43200
caacgtcagg tcgtacagtt tacccgccaa cgagaaggta ttagcggcgc gaccgcgctc    43260
aacaaatgcc acgctgttat tcccc                                         43285

<210> SEQ ID NO 2
<211> LENGTH: 24
<212> TYPE: DNA
<213> ORGANISM: Artificial Sequence
<220> FEATURE:
<223> OTHER INFORMATION: Synthetic construct

<400> SEQUENCE: 2
gtcgtgactg ggaaaacccct ggcg                                               24

<210> SEQ ID NO 3
<211> LENGTH: 24
<212> TYPE: DNA
<213> ORGANISM: Artificial Sequence
<220> FEATURE:
<223> OTHER INFORMATION: Synthetic construct

<400> SEQUENCE: 3
tcctgtgtga aattgttatc cgct                                                24
```

METHOD FOR PREVENTION AND TREATMENT OF *SALMONELLA* INFECTION

CROSS-REFERENCE TO RELATED APPLICATIONS

This application is a divisional of U.S. patent application Ser. No. 13/176,458, filed Jul. 5, 2011, which is hereby incorporated in its entirety and for all purposes.

FIELD

The present invention relates to a composition applicable for prevention or treatment of *Salmonella* infection comprising bacteriophage that is capable of destroying *Salmonella* once infected to *Salmonella* as an active ingredient and a method for prevention and treatment of *Salmonella* infection by using the said composition. That is, the present invention relates to a composition used for the purpose of prevention or treatment of *Salmonella* infection and a method for prevention and treatment of *Salmonella* infection using the same.

BACKGROUND

*Salmonella* is similar to *E. coli* in the aspects of morphology or physiology but is categorized in an independent genus for the convenience in clinical use by the proposal of K. Kauffmann et al. *Salmonella* has been isolated from enteritis and gastroenteritis patients and from animals with diverse diseases since *Salmonella choleraesuis* was first isolated from a pig died of hog cholera by Salmon and Smith in 1885. *Salmonella* has also been isolated from health animals such as chicken, cow, pig, goat, dog, and cat and from our environment.

More than 2,000 serotypes of *Salmonella* have been reported so far and it can be largely divided into two groups, one of which is the group that has host specificity and the other of which is the group that does not have host specificity. *Salmonella* is a genus of rod-shaped, Gram-negative and non-spore-forming It is a parasite living in a variety of animals.

*Salmonella* infectious disease is developed in different forms. Enteritis is the most general form of *Salmonella* infection. Once infected with *Salmonella*, such symptoms as rough skin, anorexia, conjunctivitis, depression, pale feces, spleen enlargement, and even death are observed.

Various drugs have been used for the treatment of *Salmonella* infection. However, those drugs known so far cannot lead complete cure. So, it is more important to prevent the infection than to treat it.

Damage in livestock industry caused by *Salmonella* infection is rather huge. Therefore, it is an urgent request to develop a method for prevention and effective treatment of *Salmonella* infection.

The utilization of bacteriophage is now highly drawing our attention as an effective way of treating bacterial disease. In particular, our interests in bacteriophage grow with the preference of nature-friendly method. Bacteriophage is an extremely small microorganism infecting bacteria, which is generally called phage in short. Bacteriophage is an obligate intracellular parasite that multiplis inside bacteria by making use of some or all of the host biosynthetic machinery. Upon completion of the multiplication, offspring bacteriophages are coming out of the host cell with destroying the host bacteria. The infection of bacteriophage in bacteria is very unique and specific, so only specific bacteria can be infected with a specific bacteriophage. That is, there is a limitation in bacteria that can be infected with bacteriophage. Thus, bacteriophage can only kill specific target bacteria without effecting on any other bacteria.

Bacteriophage was first found in 1915 when English bacteriologist Twort was studying on the phenomenon that micrococcus colony was being melted clearly by some reasons. And also, French bacteriologist d'Herelle noticed that *Shigella disentriae* was melted by something in filtrate of dysentery patient's feces and afterwards he separated bacteriophage independently by the following study and named it bacteriophage which meant 'eating bacteria'. Since then, bacteriophages corresponding to different pathogenic bacteria including *Shigella, Salmonella* and *Vibrio cholerae* have been continuously reported.

Owing to its capability of killing bacteria, bacteriophage has been in the center of our interest to fight with bacterial infection and studies followed thereon. However, since Flemming found out penicillin, antibiotics have been supplied and the study on bacteriophage has been limited in some east European countries and old Soviet Union. It was not until 2000 that the conventional antibiotics demonstrated their problems in use because of increasing antibiotic-resistant bacteria. So, once again, bacteriophage draws out attention as an alternative anti-bacterial agent that can take the place of the conventional antibiotics.

Therefore, the present inventors tried to develop a composition for prevention or treatment of *Salmonella* infection by using bacteriophage that can destroy *Salmonella* selectively and further tried to establish a method for prevention and treatment of *Salmonella* infection using the same. At last, the inventors isolated a proper bacteriophage from the nature and secured the gene sequence of its genome for the distinguishment from other bacteriophages. Then, the present inventors succeeded in developing a composition comprising the said bacteriophage as an active ingredient and further completed this invention by confirming that the said composition of the invention can be effectively used for prevention and treatment of *Salmonella* infection.

DISCLOSURE

Technical Problem

It is an object of the present invention to provide a novel bacteriophage capable of killing *Salmonella* selectively.

It is another object of the present invention to provide a composition usable for prevention of *Salmonella* infection comprising the said bacteriophage as an active ingredient which is capable of killing *Salmonella* selectively by infecting *Salmonella* and to provide a method for prevention of *Salmonella* infection using the same.

It is also an object of the present invention to provide a composition usable for treatment of *Salmonella* infection comprising the said bacteriophage as an active ingredient which is capable of killing *Salmonella* selectively by infecting *Salmonella* and to provide a method for treatment of *Salmonella* infection using the same.

It is further an object of the present invention to provide a disinfectant for treatment of *Salmonella* using the said composition.

It is also an object of the present invention to provide a drinking water additive using the said composition.

It is also an object of the present invention to provide a feed additive using the said composition.

Technical Solution

The present invention provides a composition comprising bacteriophage as an active ingredient which is capable of destroying *Salmonella* by infecting *Salmonella*, and a method for prevention and treatment of *Salmonella* infection by using the said composition.

Bacteriophage used as the active ingredient in the composition of the present invention is bacteriophage SP-1 having DNA represented by SEQ. ID. NO: 1 as its genome. Bacteriophage SP-1 was isolated by the present inventors and deposited at Korean Collection for Type Cultures, Korea Research Institute of Bioscience and Biotechnology on Jul. 30, 2010 (Accession No: KCTC 11737BP).

The present invention also provides a disinfectant, a drinking water additive, and a feed additive that can be used for prevention or treatment of *Salmonella* infection. Bacteriophage SP-1 included in the composition of the present invention is able to kill *Salmonella* effectively, so that it can have a preventive and/or treating effect on diverse infectious diseases caused by *Salmonella*. Therefore, the composition of the present invention can be used for the purpose of prevention and treatment of disease caused by *Salmonella*.

The pharmaceutical composition of the present invention can be used for prevention and treatment of salmonellosis, the representative disease caused by *Salmonella* including enteritis, Bacteremia, Fowl typhoid, Pullorum disease, and cholera. The term "salmonellosis" in this invention generally indicates all the symptoms caused by *Salmonella* infection including fever, headache, diarrhea, vomiting, etc.

The term "treat" or "treatment" in this description indicates (i) to suppress disease caused by *Salmonella*; and (ii) to relieve disease symptoms caused by *Salmonella*.

The representative *Salmonella* targeted by this invention is exemplified by *Salmonella Enteritidis, Salmonella Gallinarum, Salmonella Pullorum, Salmonella Typhimurium, Salmonella Choleraesuis, Salmonella Dubulin*, and *Salmonella Durby*, but not always limited thereto.

The composition of the present invention can include pharmaceutically acceptable carriers such as lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate and mineral oil, but not always limited thereto. The composition of the present invention can additionally include lubricants, wetting agents, sweetening agents, flavors, emulsifiers, suspensions and preservatives. The composition of the present invention contains bacteriophage SP-1 as an active ingredient. At this time, the bacteriophage SP-1 is included at the concentration of $1\times10^1$ pfu/mL-$1\times10^{30}$ pfu/mL or $1\times10^1$ pfu/g-$1\times10^4$ pfu/g, and more preferably at the concentration of $1\times10^4$ pfu/mL-$1\times10^{15}$ pfu/mL or $1\times10^4$ pfu/g-$1\times10^{15}$ pfu/g.

The composition of the present invention can be formulated by the method that can be performed by those in the art by using a pharmaceutically acceptable carrier and/or excipient in the form of unit dose or in multi-dose containers. The formulation can be in the form of solution, suspension, or emulsion in oil or water-soluble medium, extract, powder, granule, tablet or capsule. At this time, a dispersing agent or a stabilizer can be additionally included.

The composition of the present invention can be produced in the form of a disinfectant, a drinking water additive, and a feed additive, but not always limited thereto.

Advantageous Effect

The composition of the present invention and the method for prevention and treatment of *Salmonella* infection using the same have an advantage of high specificity against *Salmonella*, compared with other conventional chemical compositions and methods using thereof. That is, this composition does not have any effect on other useful resident flora and can be used only for the purpose of prevention and treatment of *Salmonella* infection. Thus, side effects are hardly accompanied. In general, when other chemicals such as the conventional antibiotics are used, general resident bacteria are also targeted and destroyed, resulting in the decrease of immunity in animals and bringing other side effects. In the meantime, the present invention provides an advantage of nature-friendly effect by using the composition containing natural bacteriophage as an active ingredient.

DESCRIPTION OF DRAWINGS

The application of the preferred embodiments of the present invention is best understood with reference to the accompanying drawings, wherein.

MODE FOR INVENTION

Figure 1:
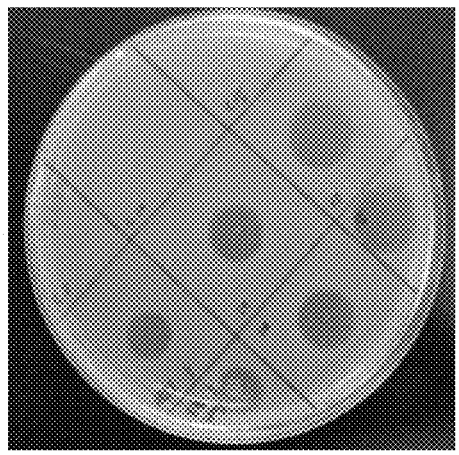
FIG. 1 is a photograph showing the result of killing activity test with bacteriophage SP-1 to *Salmonella Enteritidis*.
Figure 2:
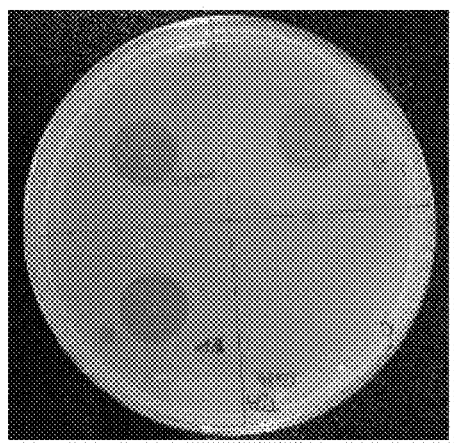
FIG. 2 is a photograph showing the result of killing activity test with bacteriophage SP-1 to *Salmonella Gallinarum*.
Figure 3:
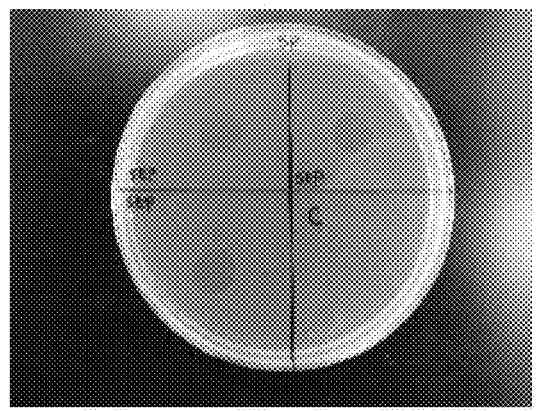
FIG. 3 is a photograph showing the result of killing activity test with bacteriophage SP-1 to *Salmonella Pullorum*.
Figure 4:
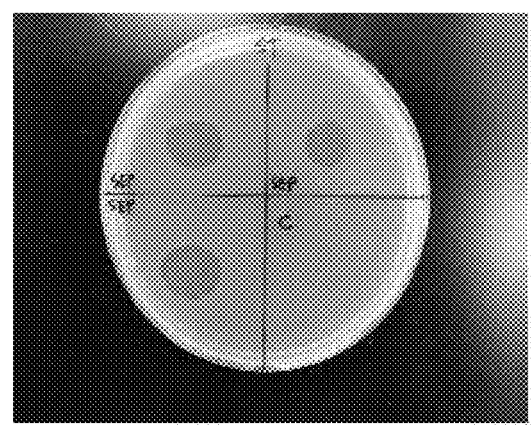
FIG. 4 is a photograph showing the result of killing activity test with bacteriophage SP-1 to *Salmonella Typhimurium*.
Figure 5:
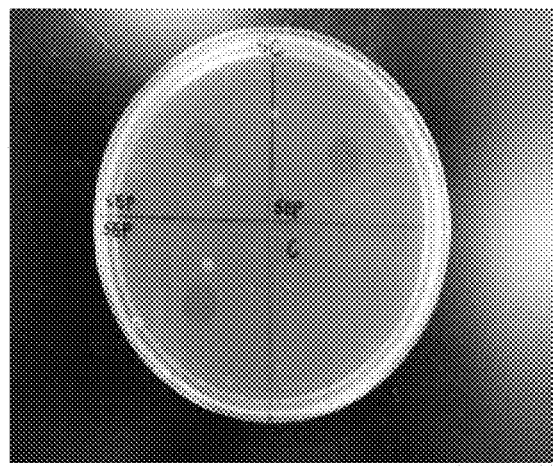
FIG. 5 is a photograph showing the result of killing activity test with bacteriophage SP-1 to *Salmonella Choleraesuis*.
Figure 6:
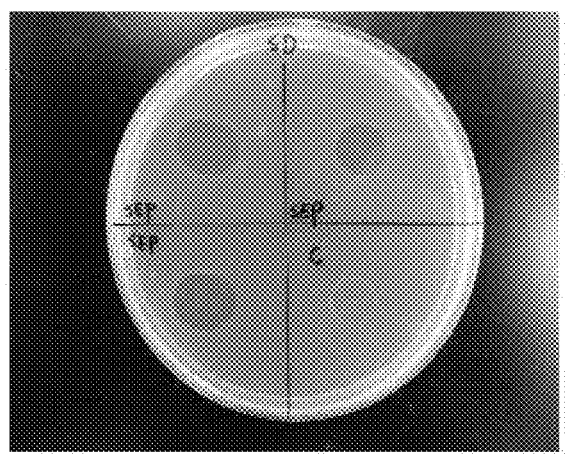
FIG. 6 is a photograph showing the result of killing activity test with bacteriophage SP-1 to *Salmonella Dubulin*.
Figure 7:
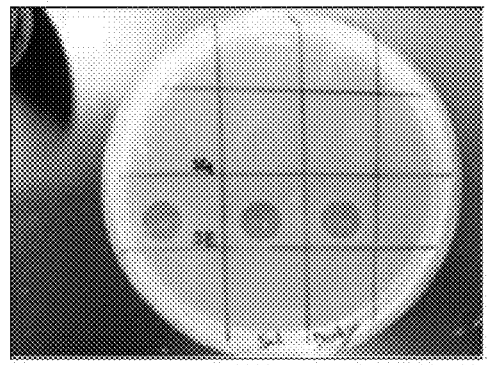
FIG. 7 is a photograph showing the result of killing activity test with bacteriophage SP-1 to *Salmonella Durby*.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Isolation of Bacteriophage that can Destroy *Salmonella*

Bacteriophage that can destroy *Salmonella* was isolated from the nature or from animal samples. In the bacteriophage isolation, *Salmonella Enteritidis* was used as the representative *Salmonella*. This *Salmonella Enteritidis* (SE51) was isolated previously by the present inventors and then identified as *Salmonella Enteritidis* by the inventors.

Collected samples were loaded in TSB (Tryptic Soy Broth) medium (casein digest, 17 g/L; soybean digest, 3 g/L; dextrose, 2.5 g/L; NaCl, 5 g/L; dipotassium phosphate, 2.5 g/L) inoculated with *Salmonella Enteritidis* (1/1000), followed by shaking culture for 3-4 hours at 37° C. Upon completion of the culture, centrifugation was performed at 8,000 rpm for 20 minutes and the supernatant was recovered. *Salmonella* was inoculated in the recovered supernatant (1/1000), followed by shaking culture for 3-4 hours at 37° C. This procedure was repeated 5 times in total in order to increase bacteriophage titer if bacteriophage was included in the sample. After repeating the process 5 times, the culture solution proceeded to centrifugation at 8,000 rpm for 20 minutes. Then, the supernatant was filtered using 0.45 μm filter. The obtained filtrate was investigated by using general spot assay to see whether bacteriophage that could kill *Salmonella* was included.

Spot assay was performed as follows. *Salmonella* was inoculated in TSB medium (1/1000), followed by shaking culture at 37° C. overnight. Then, 3 mL of the obtained *Salmonella* culture solution ($OD_{600}$: 2.0) was spread on TSA (Tryptic Soy Agar) plate medium (casein digest, 15 g/L; soybean digest, 5 g/L; NaCl, 5 g/L; agar, 15 g/L). The plate medium stayed on clean bench for about 30 minutes to let the spread solution is dried. After drying, 10 nl of the prepared filtrate was loaded on the plate medium whereon *Salmonella* was spread, which was dried as it is for 30 minutes. After drying, the plate medium was standing cultured at 37°C. for a day. It was then investigated whether the clear zone was formed on the spot where the filtrate was loaded. If the clear zone was formed thereon, it suggested that bacteriophage that could kill *Salmonella* was included therein. According to this procedure, the filtrate containing bacteriophage that could destroy *Salmonella* could be obtained.

Pure bacteriophage was isolated from the filtrate confirmed to contain the bacteriophage capable of killing *Salmonella*. The isolation of pure bacteriophage was performed by plaque assay. More precisely, one of plaques formed from plaque assay was recovered by using a sterilized tip, which was then added to *Salmonella* culture solution, followed by culture for 4-5 hours. Upon completion of the culture, centrifugation was performed at 8,000 for 20 minutes to obtain supernatant. *Salmonella* culture solution was added to the obtained supernatant at the ratio of 1:50, followed by further culture for 4-5 hours. To increase the number of bacteriophage, this procedure was repeated at least 5 times and then centrifugation was performed at 8,000 for 20 minutes to obtain supernatant. Plaque assay was performed with the supernatant. Generally, pure bacteriophage separation cannot be accomplished simply by performing the above procedure once. Thus, the previous steps were repeated again using one of plaques formed from plaque assay. After repeating the procedure at least 5 times, the solution comprising pure bacteriophage was obtained. The repetition of this pure bacteriophage separation processes was not finished until the sizes and shapes of plaques were all similar. Pure bacteriophage separation was confirmed at last by observing under electron microscope. If pure bacteriophage was not confirmed, the above processes were repeated again.

The preparation of bacteriophage suspension was performed as follows. *Salmonella* culture solution was added to the solution comprising pure bacteriophage at the ratio of 1:50, followed by culture for 4-5 hours. Upon completion of the culture, centrifugation was performed at 8,000 rpm for 20 minutes to obtain supernatant. To obtain enough amount of bacteriophage, the said process was repeated 5 times in total. The final supernatant was filtered with 0.45 μm filter, followed by precipitation by using polyethylene glycol (PEG). Particularly, PEG and NaCl were added to 100 mL of the filtrate (10% PEG 8000/0.5 M NaCl), which stood at room temperature for 2-3 hours. Then, centrifugation was performed at 8,000 rpm for 30 minutes to obtain bacteriophage precipitate. The obtained bacteriophage precipitate was suspended in 5 mL of buffer (10 mM Tris-HCl, 10 mM $MgSO_4$, 0.1% Gelatin, pH 8.0). This suspension was called bacteriophage suspension or bacteriophage solution.

At last, purified pure bacteriophage was obtained and this bacteriophage was named bacteriophage SP-1, which was then deposited at Korean Collection for Type Cultures, Korea Research Institute of Bioscience and Biotechnology on Jul. 30, 2010 (Accession No: KCTC 11737BP).

EXAMPLE 2

Extraction of Bacteriophage SP-1 Genome and Sequencing Thereof

Bacteriophage SP-1 genome was extracted as follows using the bacteriophage suspension obtained in Example 1. To eliminate *Salmonella* DNA and RNA which might be included in the suspension, DNase I and RNase A were added to 10 mL of the bacteriophage suspension (200 U each), which stood at 37°C. for 30 minutes. 30 minutes later, to neutralize DNase I and RNase A activity, 500 μL of 0.5 M ethylenediaminetetraacetic acid (EDTA) was added, which stood for 10 minutes. The solution stood at 65°C. for another 10 minutes, then 100 μL of proteinase K (20 mg/mL) was added, followed by reaction at 37°C. for 20 minutes to break the outer wall of the bacteriophage. Then, 500 μL of 10% sodium dodecyl sulfate (SDS) solution was added thereto, followed by reaction at 65°C. for one hour. One hour later, 10 μL of the mixed solution comprising phenol:chloroform:isoamylalcohol at the concentration ratio of 25:24:1 was added thereto and the solution was well mixed. Centrifugation was performed at 13,000 rpm for 15 minutes to separate layers, among which the upper most layer was obtained. Isopropyl alcohol was added to the obtained layer at the volume ratio of 1.5, followed by centrifugation at 13,000 rpm for 10 minutes to precipitate genome. The precipitate was recovered, to which 70% ethanol was added, flowed by centrifugation at 13,000 rpm for 10 minutes. The washed precipitate was collected and vacuum-dried, which was then dissolved in 100 μL of water.

Sequencing was performed with the obtained genome as follows. Particularly, gene fragments were obtained by digesting gDNA, the bacteriophage SP-1 genome, with Hpa II according to the conventional method. Linear vector fragment which would be used for the insertion of the gene fragments was also prepared by treating pBluescript II SK(+) phagemid vector (Stratagene) with Cla I. The prepared gene fragments and the vector fragment were ligated by using T4 ligase according to the conventional method. The resultant recombinant vector containing the bacteriophage SP-1 gene fragment was introduced into Top 10F' (Invitrogen), a kind of *E. coli*, by eletroporation (electro-transformation). The transformant was selected on agar plate medium containing X-Gal (5-bromo-4-chloro-3-indolyl-beta-D-galactopyranoside), IPTG (isopropyl β-D-1-thiogalactopyranoside) and ampicillin by the conventional Blue-White colony selection method. The selected single colony was inoculated on the culture medium supplemented with ampicillin, followed by shaking culture for overnight. Plasmid was extracted from the cultured cells by using plasmid purification kit (iNtRON Biotechnology, Korea). The extracted plasmid proceeded to electrophoresis using 0.8% agarose gel to measure the size.

Finally the recombinant plasmid was obtained. The clone containing the obtained plasmid was cultured again and then plasmid was extracted from the cultured cells again. Sequencing with the extracted plasmid was performed by using M13 forward primer and M13 reverse primer which have been generally used. The sequence of each primer is as follows.

TABLE 1

| Primer | Sequence |
|---|---|
| M13 forward primer | SEQ. ID. NO: 2 GTCGTGACTGGGAAAACCCTGGCG |
| M13 reverse primer | SEQ. ID. NO: 3 TCCTGTGTGAAATTGTTATCCGCT |

Partial gene sequences of the bacteriophage SP-1 genome were identified by the above method, based on which total gene sequencing was performed according to the conventional method. The identified bacteriophage SP-1 gene sequence was represented by SEQ. ID. NO: 1.

Based on the gene sequence of bacteriophage SP-1, similarity to those sequences of the conventional bacteriophages was investigated by using BLAST (http://www.ncbi.nlm.nih.gov/BLAST/). As a result, the nucleotide sequence of bacteriophage SP-1 had high similarity to those of bacteriophage SS3e (GenBank Accession No. AY730274) and Salmonella phage SETP3 (GenBank Accession No. EF177456). Particularly, the nucleotide sequence of the bacteriophage SP-1 genome was closer to the nucleotide sequence of the bacteriophage SS3e. However, the size of the bacteriophage SP-1 genome was 43285 bp, while the size of the bacteriophage SS3e genome was 40794 bp, suggesting that the bacteriophage SP-1 genome was larger. The additional nucleotides in the bacteriophage SP-1 showed high similarity to some of the Salmonella phage SETP3 genome sequence. Among the additional nucleotides in the bacteriophage SP-1, two open reading frames (ORF) were identified.

These ORFs had no similarity to ORFs of the bacteriophage SS3e genome. Instead, they demonstrated similarity to those of the Salmonella phage SETP3 genome. However, while those ORFs were similar to the ORF like sequence in the Salmonella phage SETP3, one of them showed higher similarity to the ORF found in the E. coli phage Klindl genome (GenBank Accession No. GU196279.1).

The above results indicate that the genome of the bacteriophage SP-1 shows combined characteristics of both bacteriophage SS3e and Salmonella phage SETP3. Moreover, it could be assumed that other additional characteristics could be included except the said combined characteristics. Therefore, it can be concluded that the bacteriophage SP-1 is a novel bacteriophage which is completely different from any of the conventional bacteriophages.

EXAMPLE 3

Killing Activity of Bacteriophage SP-1 to Various Salmonella Bacteria

Various Salmonella bacteria were used to investigate killing activity of the selected bacteriophage SP-1. For the investigation, clear zone formation was first observed by spot assay by the same manner as described in Example 1. Salmonella bacteria used for this assay were Salmonella Enteritidis (SE51), Salmonella Gallinarum (SG36), Salmonella Pullorum (SP-11), Salmonella Typhimurium (ST2), Salmonella Choleraesuis (ATCC 9120), Salmonella Dubulin (BA584), and Salmonella Durby. Salmonella Choleraesuis (ATCC 9120) was the standard strain, and Salmonella Dubulin (BA584) and Salmonella Durby were the isolates distributed from National Veterinary Research & Quarantine Service Korea. Salmonella Enteritidis (SE51), Salmonella Gallinarum (SG36), Salmonella Pullorum (SP-11), and Salmonella Typhimurium (ST2) were the isolates isolated and identified by the inventors. The results of the related experiments are shown in FIG. 1-FIG. 7. As shown in FIG. 1-FIG. 7, the bacteriophage SP-1 was confirmed to have Salmonella killing activity against various Salmonella bacteria. In addition, killing activity of the bacteriophage SP-1 to Actinobacillus pleuropneumoniae, Bordetella bronchiseptica, Enterococcus faecalis, Enterococcus faecium, Escherichia coli, Streptococcus agalactiae, Streptococcus mitis, Streptococcus uberis and Pseudomonas aeruginosa was further investigated. As a result, it was confirmed that the bacteriophage SP-1 did not have killing activity against those bacteria.

From the above results, it was confirmed that the bacteriophage SP-1 can be used as an active ingredient of the composition formulated for the purpose of prevention and treatment of Salmonella infection.

EXAMPLE 4

Application Example of Bacteriophage SP-1 for Prevention of Salmonella Infection 100 µL of bacteriophage SP-1 suspension ($1\times10^8$ pfu/mL) was loaded to 7 tubes each containing 9 mL of TSB medium. Another 7 tubes containing 9 mL of TSB medium alone were also prepared. One of those 7 tubes containing medium and bacteriophage suspension and one of those 7 tubes containing medium alone are paired for one experimental group. To the prepared 7 experimental groups were added Salmonella Enteritidis, Salmonella Gallinarum, Salmonella Pullorum, Salmonella Typhimurium, Salmonella Choleraesuis, Salmonella Dubulin, and Salmonella Durby culture solution ($OD_{600}$: 0.5), respectively. After Salmonella bacteria were added to those tubes, they were all transferred to 37° C. incubator, followed by shaking culture, during which the growth of Salmonella was observed. As shown in Table 2, the growth of Salmonella was suppressed in the tubes containing bacteriophage SP-1 suspension in every experimental group. In the meantime, the growth of Salmonella was not inhibited in the bacteriophage free tubes.

TABLE 2

Suppression of Salmonella growth

| | | $OD_{600}$ | | |
|---|---|---|---|---|
| | | Culture 0 min. | culture 15 min. | culture 60 min |
| Salmonella Enteritidis | Bacteriophage− | 0.5 | 0.7 | 1.5 |
| | Bacteriophage+ | 0.5 | 0.1 | 0.05 |
| Salmonella Gallinarum | Bacteriophage− | 0.5 | 0.65 | 1.4 |
| | Bacteriophage+ | 0.5 | 0.1 | 0.05 |
| Salmonella | Bacteriophage− | 0.5 | 0.8 | 1.6 |

TABLE 2-continued

Suppression of *Salmonella* growth

| | | $OD_{600}$ | | |
|---|---|---|---|---|
| | | Culture 0 min. | culture 15 min. | culture 60 min |
| Pullorum | Bacteriophage+ | 0.5 | 0.1 | 0.05 |
| Salmonella | Bacteriophage− | 0.5 | 0.75 | 1.5 |
| Typhimurium | Bacteriophage+ | 0.5 | 0.1 | 0.05 |
| Salmonella | Bacteriophage− | 0.5 | 0.65 | 1.3 |
| Choleraesuis | Bacteriophage+ | 0.5 | 0.1 | 0.05 |
| Salmonella | Bacteriophage− | 0.5 | 0.7 | 1.35 |
| Dubulin | Bacteriophage+ | 0.5 | 0.1 | 0.05 |
| Salmonella | Bacteriophage− | 0.5 | 0.7 | 1.5 |
| Durby | Bacteriophage+ | 0.5 | 0.1 | 0.05 |

The above results indicate that the bacteriophage SP-1 of the present invention not only suppresses the growth of various *Salmonella* bacteria but also even destroys them, so that it can be used as an active ingredient for the composition formulated for the purpose of prevention of *Salmonella* infection.

EXAMPLE 5

Treatment Example 1 of *Salmonella* Infectious Disease using Bacteriophage SP-1

4 chicks at 2 days of age were administered with $1\times10^7$ cfu of *Salmonella Enteritidis* to induce infection forcefully (animal 1-1, animal 1-2, animal 1-3, animal 1-4). Another 4 chicks at 2 days of age were administered with $1\times10^7$ cfu of *Salmonella Choleraesuis* to induce infection forcefully (animal 2-1, animal 2-2, animal 2-3, animal 2-4). Animal 1-1, animal 1-2, animal 2-1, and animal 2-2 were forced to eat the feed containing bacteriophage SP-1 (mixed at the concentration of $1\times10^9$ pfu/g feed), while animal 1-3, animal 1-4, animal 2-3, and animal 2-4 were given with bacteriophage free feed. 2 days later, the numbers of *Salmonella* bacteria in feces and caecum contents were counted. To avoid contamination by other bacteria, *Salmonella* selective medium (Rambach agar plate; Merck) was used for the counting. As a result, in those animals fed with bacteriophage SP-1 mixed feed, at least 1000 times less *Salmonella* was detected in feces, compared with that in the control. In caecum contents, at least 200 times less *Salmonella* was detected in those animals fed with bacteriophage SP-1 mixed feed.

From the above results, it was confirmed that the bacteriophage SP-1 of the present invention was very effective in treating *Salmonella* infection.

EXAMPLE 6

Treatment Example 2 of *Salmonella* Infectious Disease using Bacteriophage SP-1

Figure 8:
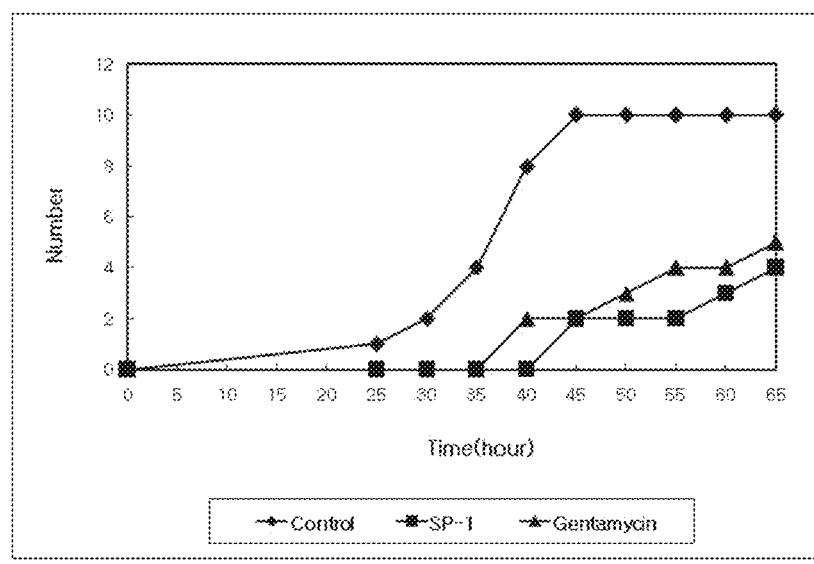
FIG. 8 is a graph illustrating the result of chick test. "Number" of Y axis indicates the number of dead chicks. "Control" indicates those chicks administered with *Salmonella Gallinarum* alone. "SP-1" indicates those chicks treated with bacteriophage SP-1 of the present invention and "Gentamycin" indicates those chicks treated with gentamycin.

In this example, it was investigated how much bacteriophage SP-1 could reduce the death of chicks infected with *Salmonella*. *Salmonella Gallinarum*, which was the pathogen of fowl typhoid, was used for the experiment. 10 broiler chickens at 2 days of age were grouped as one, and three groups were prepared in total. All the groups were orally administered with *Salmonella Gallinarum* suspension ($1\times10^7$ cfu). 10 hours after the administration, the experimental group chicks were orally administered with bacteriophage SP-1 suspension ($1\times10^9$ pfu). Bacteriophage SP-1 suspension was additionally administered orally twice at 24 hours interval after the first administration. The positive control group was prepared by administering the antibiotics, gentamycin (5 mg/kg), to the animals via muscular injection 10 hours after the *Salmonella Gallinarum* administration. The gentamycin injection was also repeated twice. The remaining one group was prepared as the negative control which was not treated with anything. As shown in FIG. 8, the lifespan of the animal treated with bacteriophage SP-1 suspension was significantly extended, compared with that of the negative control. Even if complete cure might not be achieved, significant treatment effect of bacteriophage SP-1, which was shown as significantly extended lifespan, was not in doubt, considering that, unlike the natural infection, excessive amount of bacteria was forcefully administered directly to the animal to cause infectious disease at a severe level.

From the above results, it was confirmed that the bacteriophage SP-1 of the present invention was very effective in treating *Salmonella* infection.

EXAMPLE 7

Preparation of Feed Additive and Feed

Feed additive containing bacteriophage SP-1 at the concentration of $1\times10^9$ pfu/g was prepared with bacteriophage SP-1 suspension. The preparation method was as follows. Bacteriophage SP-1 suspension was evenly sprayed on maltodextran at the proper weight ratio, which was then vacuum-dried at room temperature, followed by pulverization into fine powders. Silica was added thereto at the weight ratio of 5% and the mixture was well mixed. For the drying process, either reduced pressure drying, drying at elevated temperature, or freeze drying can be used. For the control, bacteriophage free feed additive was also prepared by spraying buffer which was used for the preparation of bacteriophage suspension instead of bacteriophage suspension.

The above two feed additives were mixed with feed for pig respectively at the weight ratio of 1:1,000. As a result, two different kinds of feeds for pig were prepared. Another two different feed additives were also prepared by the same manner as described above, which were mixed with feed for poultry farming respectively at the weight ratio of 1:1,000. As a result, two different feeds for poultry farming were prepared.

EXAMPLE 8

Preparation of Drinking Water Additive and Disinfectant

Drinking water additive and disinfectant are prepared by the same method because both are formulated in the same form and have only difference in their use. Drinking water additive (or disinfectant) containing bacteriophage SP-1 at the concentration of $1\times10^9$ pfu/mL was prepared. The method of preparation of drinking water additive (or disinfectant) is as follows. Bacteriophage SP-1 was added to the buffer which was generally used for the preparation of bacteriophage suspension at the concentration of $1\times10^9$ pfu/mL and well mixed. For the control, the buffer itself was used as the bacteriophage free drinking water additive (or disinfectant).

The prepared two different drinking water additives (or disinfectants) were diluted with water at the ratio of 1:1,000, resulting in the final drinking water additive or disinfectant.

EXAMPLE 9

Investigation of Feeding Efficacy on Pig Farming

Improvement of feeding efficacy on pig farming was investigated by using the feeds, drinking water and disinfectants prepared in Examples 7 & 8. In particular, this investigation was performed by observing death rate. 30 piglets were divided into three groups (10 piglets/group) (group A: supplied with bacteriophage by the feeds; group B: supplied with bacteriophage by the drinking water; group C: treated with the disinfectants containing bacteriophage). The investigation was performed for 4 weeks. Each group was divided into two subgroups of 5 piglets. Those subgroups were either treated with bacteriophage SP-1 (subgroup (1)) or not treated with bacteriophage SP-1 (subgroup (2)). The test piglets were 20 days old. Each group piglets were raised in an isolated cage separated from each other at regular intervals. Each subgroup was sorted and marked as shown in Table 3.

TABLE 3

Subgroup sorting and marking in feeding efficacy test on pig farming

|  | Subgroup sorting and marking | |
| --- | --- | --- |
|  | Bacteriophage SP-1+ | Bacteriophage SP-1− |
| Feed | A-(1) | A-(2) |
| Drinking water | B-(1) | B-(2) |
| Disinfectant | C-(1) | C-(2) |

The piglets were supplied with the feeds prepared in Example 7 and the drinking water prepared in Example 8 according to the conventional method as shown in Table 3. Disinfection was performed with the conventional disinfectant and the disinfectant of the present invention by taking turns, three times a week. The day when the disinfectant of the present invention was sprayed on, the conventional disinfectant was not used. The results are shown in Table 4.

TABLE 4

| Group | Death Rate (%) |
| --- | --- |
| A-(1) | 0 |
| A-(2) | 20 |
| B-(1) | 0 |
| B-(2) | 40 |
| C-(1) | 0 |
| C-(2) | 20 |

From the above results, it was confirmed that the feeds, drinking water and disinfectants prepared according to the present invention could help to reduce death rate in pig farming Therefore, it was concluded that the composition of the present invention was effective in the improvement of feeding efficacy on pig farming.

EXAMPLE 10

Investigation of Feeding Efficacy on Chicken Farming

*Salmonella* is also an important pathogen of chicken disease. So, the effect of the composition of the present invention on chicken farming was also investigated. Improvement of feeding efficacy on chicken farming was investigated by using the feeds, drinking water and disinfectants for chicken farming prepared in Examples 7 & 8. In particular, this investigation was performed by observing death rate. 60 chicks at 2 days of age were divided into three groups (20 chicks/group) (group A: supplied with bacteriophage by the feeds; group B: supplied with bacteriophage by the drinking water; group C: treated with the disinfectants containing bacteriophage). The investigation was performed for 4 weeks. Each group was divided into two subgroups of 10 chicks. Those subgroups were either treated with bacteriophage SP-1 (subgroup [1]) or not treated with bacteriophage SP-1 (subgroup [2]). The chicks were isolated group by group and raised. Each subgroup was sorted and marked as shown in Table 5.

TABLE 5

Subgroup sorting and marking in feeding efficacy test on chicken farming

|  | Subgroup sorting and marking | |
| --- | --- | --- |
|  | Bacteriophage SP-1+ | Bacteriophage SP-1− |
| Feed | A-[1] | A-[2] |
| Drinking water | B-[1] | B-[2] |
| Disinfectant | C-[1] | C-[2] |

The chicks were supplied with the feeds for chicken farming prepared in Example 7 and the drinking water for chicken farming prepared in Example 8 according to the conventional method as shown in Table 5. Disinfection was performed with the conventional disinfectant and the disinfectant of the present invention by taking turns, three times a week. The day when the disinfectant of the present invention was sprayed on, the conventional disinfectant was not used. The results are shown in Table 6.

TABLE 6

| Group | Death Rate (%) |
| --- | --- |
| A-[1] | 0 |
| A-[2] | 20 |
| B-[1] | 0 |
| B-[2] | 30 |
| C-[1] | 0 |
| C-[2] | 30 |

From the above results, it was confirmed that the feeds, drinking water and disinfectants prepared according to the present invention could help to reduce death rate in chicken farming Therefore, it was concluded that the composition of the present invention was effective in the improvement of feeding efficacy on chicken farming Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for treating *Salmonella* infections in an animal subject, comprising administering to the animal subject an effective amount of the isolated bacteriophage SP-1 having a genome comprising SEQ. ID. NO: 1 and deposited under the accession number KCTC 11737BP.

2. The method according to claim 1, wherein the *Salmonella* is *Salmonella enteritidis, Salmonella gallinarum, Salmonella pullorum, Salmonella typhimurium, Salmonella choleraesuis, Salmonella dublin,* or *Salmonella durby.*

* * * * *